US009534998B2

(12) United States Patent
Tsunoda

(10) Patent No.: US 9,534,998 B2
(45) Date of Patent: Jan. 3, 2017

(54) SYSTEM AND METHOD FOR COUNTING AEROSOL PARTICLES IN ATMOSPHERE WITH RESPECT TO EACH PARTICLE SIZE BY APPROPRIATELY SETTING RATIO OF FLOW RATE OF SAMPLE GAS AND SHEATH GAS IN DMA

(75) Inventor: Chiryo Tsunoda, Kokubunji (JP)

(73) Assignee: RION CO., LTD., Tokyo (JP)

( * ) Notice: Subject to any disclaimer, the term of this patent is extended or adjusted under 35 U.S.C. 154(b) by 1097 days.

(21) Appl. No.: 13/605,236

(22) Filed: Sep. 6, 2012

(65) Prior Publication Data

US 2013/0085706 A1    Apr. 4, 2013

Related U.S. Application Data

(60) Provisional application No. 61/531,702, filed on Sep. 7, 2011.

(51) Int. Cl.
*G01N 15/02*    (2006.01)
*G01F 1/56*    (2006.01)
(Continued)

(52) U.S. Cl.
CPC .......... *G01N 15/0266* (2013.01); *B03C 3/145* (2013.01); *B03C 3/155* (2013.01); *G01F 1/56* (2013.01);
(Continued)

(58) Field of Classification Search
CPC ... G01N 15/0266; G01N 15/0656; B03C 5/00; B03C 3/145; B03C 3/155; B03C 2201/24; G01F 1/56; G06F 15/00
(Continued)

(56) References Cited

U.S. PATENT DOCUMENTS 5,922,976 A     7/1999 Russell et al.
6,003,389 A  *  12/1999 Flagan ................. G01N 27/622
                                                    324/464

(Continued)

FOREIGN PATENT DOCUMENTS

JP          4710787 B2      6/2011

OTHER PUBLICATIONS

U.S. Appl. No. 13/605,183, filed Sep. 6, 2012; First Named Inventor: Chiryo Tsunoda; Title: "Apparatus and Method for Detecting Aerozol Particles in Atmosphere and Counting Aerozol Particles with Respect to Each Particle Size".

*Primary Examiner* — Alexander Satanovsky
*Assistant Examiner* — Lina Cordero
(74) *Attorney, Agent, or Firm* — Holtz, Holtz & Volek PC

(57) ABSTRACT

A maximum number of charges on aerosol particles which are measurement targets is decided as a natural number x equal to or larger than 2. First and second electrical mobility groups are derived based on x. The first group includes electrical mobility $Zc(U)$ and electrical mobilities having voltage values equal to a voltage U multiplied by values from 2 to x respectively, and the second group includes electrical mobilities having respective voltage values equal to voltage U multiplied by irreducible fractions which are coprime to each other among values with regularity. A ratio of flow rate with which range corresponding to the electrical mobilities included in the first group do not interfere with one another and the range corresponding to the electrical mobilities included in the first group and range corresponding to the electrical mobilities included in the mobility group do not interfere with one another is calculated.

8 Claims, 18 Drawing Sheets

(51) Int. Cl.
*G06F 15/00* (2006.01)
*B03C 3/145* (2006.01)
*B03C 3/155* (2006.01)
*G01N 15/06* (2006.01)

(52) U.S. Cl.
CPC ........... *G01N 15/0656* (2013.01); *G06F 15/00* (2013.01); *B03C 2201/24* (2013.01)

(58) Field of Classification Search
USPC ...................................................... 702/128
See application file for complete search history.

(56) References Cited

U.S. PATENT DOCUMENTS

| | | | | |
|---|---|---|---|---|
| 6,281,972 | B1* | 8/2001 | Ebara | G01N 15/0266 356/335 |
| 6,541,266 | B2* | 4/2003 | Modzelewski | G01N 21/8483 422/404 |
| 8,919,183 | B1* | 12/2014 | Dhaniyala | G01N 15/0266 73/28.02 |
| 2008/0047373 | A1* | 2/2008 | Ahn | G01N 15/0266 73/865.5 |
| 2009/0056535 | A1* | 3/2009 | Moosmuller | B03C 5/00 95/23 |
| 2009/0173670 | A1* | 7/2009 | Okuda | G01N 15/0266 209/127.1 |
| 2012/0001067 | A1* | 1/2012 | Orii | G01N 15/0266 250/288 |
| 2013/0060509 | A1* | 3/2013 | Tsunoda | G01N 15/0266 702/128 |

\* cited by examiner

| NUMBER OF CHARGES | SET RATIO OF FLOW RATE $\delta = \dfrac{q_2}{q_1}$ |
|---|---|
| $p = 1$ | — |
| $p = 2$ | $\delta < \dfrac{1}{3}$ |
| $p = 3$ | $\delta < \dfrac{1}{7}$ |
| $p = 4$ | $\delta < \dfrac{1}{7}$ |
| $p = 5$ | $\delta < \dfrac{1}{11}$ |
| $p = 6$ | $\delta < \dfrac{1}{11}$ |
| ⋮ | ⋮ |

FIG.17

SYSTEM AND METHOD FOR COUNTING AEROSOL PARTICLES IN ATMOSPHERE WITH RESPECT TO EACH PARTICLE SIZE BY APPROPRIATELY SETTING RATIO OF FLOW RATE OF SAMPLE GAS AND SHEATH GAS IN DMA

BACKGROUND OF THE INVENTION

Field of the Invention

The present invention relates to a system and a method for counting aerosol particles in the atmosphere with respect to each particle size, and more particularly, to a system and a method for counting the aerosol particles by appropriately setting a ratio of flow rate of sample gas and sheath gas.

Description of the Related Art

In the atmosphere, "aerosol particles" which are fine liquid or solid particles are suspended. As these aerosol particles, ISO 15900:2009 targets at aerosol particles whose particle size is 1 nm to 1 μm. To count the aerosol particles having several nm to 1 μm particle sizes, an aerosol particle measuring device is used. The aerosol particle measuring device includes, for example, a differential mobility analyzer (DMA) and a condensation particle counter (CPC), or the DMA and a Faraday cup aerosol electrometer (FCAE). The CPC or the FACE measures the aerosol particles classified out by the DMA, whereby it is possible to count the aerosol particles with respect to each particle size by using the result of the measurement.

In the case where the DMA is used for the classifying, the aerosol particles include not only singly charged aerosol particles whose particle size is relatively small but also multiply (doubly, triply, . . . ) charged aerosol particles whose particle size is relatively large. Therefore, in the measurement, it is assumed that the aerosol particles classified out by the DMA are singly charged and a lognormal distribution holds true in a relation between the particle size and quantity, and the counting result is corrected regarding the quantity of the multiply charged aerosol particles and then particle size distribution is calculated. In the correction, an approximate expression of Wiedensohler or the like is employed as an existence probability of charged number.

Generally, when the DMA is used, multiply charged particles exist for one particle size and when the classifying is performed based on the same electrical mobility, there exist multiply charged particles with different particle sizes. Further, it is known that a variation in the classifying based on the electrical mobility is influenced by flow rates of the aerosol particles and sheath gas in the DMA.

SUMMARY OF THE INVENTION

The present invention disclosed and claimed herein, in one aspect thereof, is a ratio of flow rate deciding method. This method includes: a maximum charge number deciding step of deciding a maximum number of charges on aerosol particles being measurement targets among charged aerosol particles as a natural number x equal to or larger than 2; a reference electrical mobility defining step of defining electrical mobility which is ability of aerosol particles whose number of charges is 1 among the aerosol particles being the measurement targets to move in the electric field, as $Zc(U)$ expressed with a voltage value U supplied to form the electric field; an electrical mobility group deriving step of deriving a first electrical mobility group and a second electrical mobility group based on x decided in the maximum charge number deciding step, the first electrical mobility group including the electrical mobility $Zc(U)$ and electrical mobilities expressed with voltage values equal to the voltage value U multiplied by values from 2 to x respectively, and the second electrical mobility group including electrical mobilities expressed with respective voltage values equal to the voltage value U multiplied by irreducible fractions which are coprime to each other among values with regularity which are $x/(x-1)$, $x/(x-2)$, ... $x/2$, $(x-1)/(x-2)$, $(x-1)/(x-3)$, $(x-1)/2$, $(x-2)/(x-3)$, $(x-2)/(x-4)$, ... $(x-2)/2$, ... and $3/2$; a converting step of expressing each of the electrical mobilities by using $Zc(U)$ defined in the reference electrical mobility defining step, regarding all the electrical mobilities included in the first electrical mobility group and the second electrical mobility group derived in the electrical mobility group deriving step; a range defining step of, if a range where a given electrical mobility is variable by adjusting a ratio of flow rate is defined as a range corresponding to the relevant electrical mobility, defining the range corresponding to all the electrical mobilities included in the first electrical mobility group and the second electrical mobility group derived in the electrical mobility group deriving step, after the converting step; and a final calculating step of calculating a ratio of flow rate with which the range corresponding to the electrical mobilities included in the first electrical mobility group, which range are defined in the range defining step, do not interfere with one another and the range corresponding to the electrical mobilities included in the first electrical mobility group and the range corresponding to the electrical mobilities included in the second electrical mobility group do not interfere with one another.

Further scope of applicability of the present invention will become apparent from the detailed description given hereinafter. However, it should be understood that the detailed description and specific example, while indicating preferred embodiment of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 17 is an explanatory chart of a relation between the number of charges on aerosol particles that are classified out and a ratio of flow rate.

DETAILED DESCRIPTION

Figure 1:
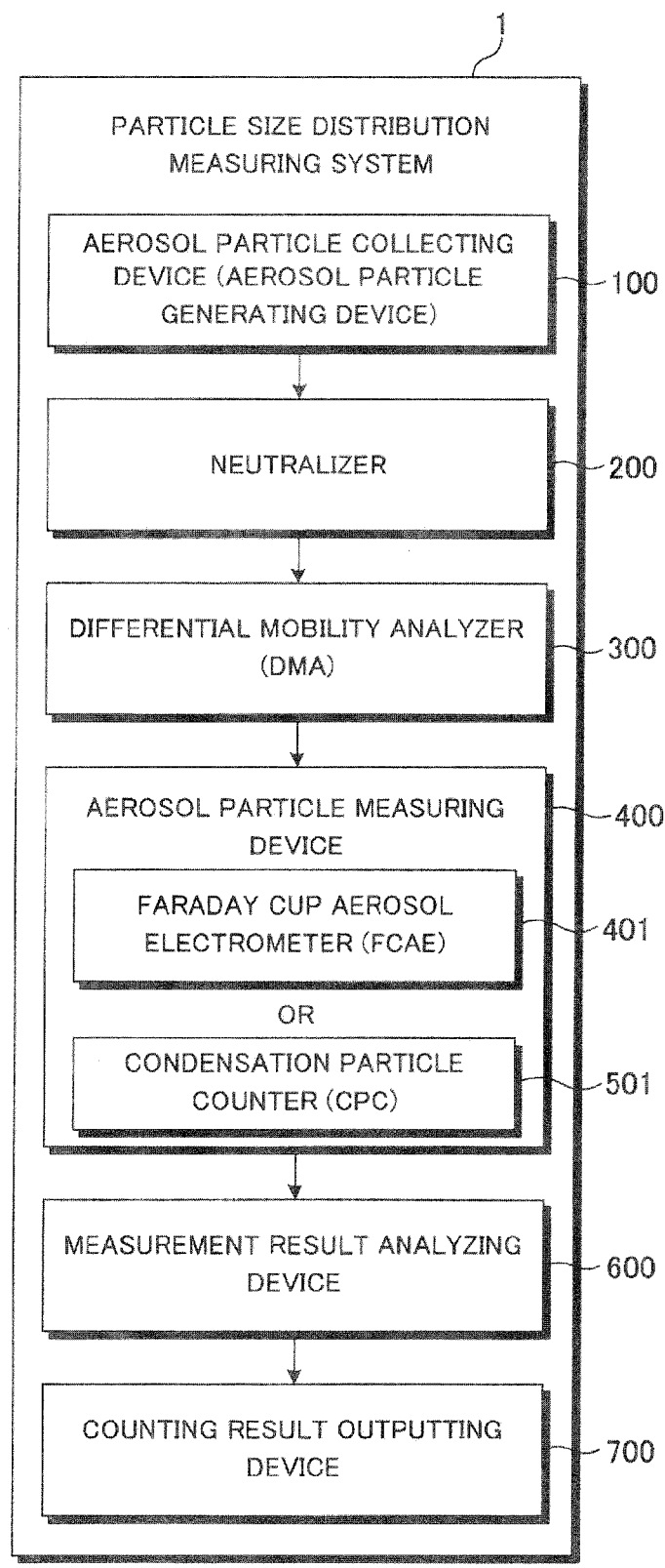
FIG. 1 is an explanatory diagram of a structure of an aerosol particle measuring device.

As shown in FIG. 1, a particle size distribution measuring system 1 includes an aerosol particle collecting device (or an aerosol particle generating device) 100, a neutralizer 200, a differential mobility analyzer (hereinafter, referred to as DMA) 300; an aerosol particle measuring device 400, and a measurement result analyzing device 600, and a counting result outputting device 700.

The aerosol particle collecting device 100 collects aerosol particles such as dust, droplets (liquid particles), and so on suspended in the atmosphere. Concretely, the aerosol particle collecting device 100 includes a dust collector which collects (catches) aerosol particles whose particle size is approximately 1 nm to approximately 1 µm.

The aerosol particle generating device 100 which is a different form from the collecting device includes a soot generator which generates soot (carbide) by utilizing a combustion process, an aerosol particle generator which generates droplets from a solvent; and so on.

Incidentally, details of particle density distribution (particle size distribution per unit volume) regarding the collected or generated dust and droplets (liquid particles) suspended in the atmosphere will be described later with reference to another drawing.

The aerosol particles collected by the aerosol particle collecting device 100 (or generated by the aerosol particle generating device 100) are next sent to the neutralizer 200.

The neutralizer 200 is a device which charges the aerosol particles collected by the aerosol collecting device 100 so that an average charge amount becomes zero (charged equilibrium state). The concrete contents approximately the aerosol particles charged by the neutralizer 200 will be further described later with reference to another drawing.

The aerosol particles charged by the neutralizer 200 (also including uncharged ones) are next sent to the DMA 300.

The DMA 300 classifies the aerosol particles charged by the neutralizer 200 according to electrical mobility. By adjusting the setting regarding the operation of the DMA 300 (for example, supplied voltage), it is possible to set the electrical mobility according to the aerosol particles being targets of the classifying. The concrete contents approximately the aerosol particles classified out by the DMA 300 will be further described later with reference to another drawing.

The aerosol particles classified out by the DMA 300 are next sent to the aerosol particle measuring device 400. Incidentally, the aerosol particles not classified out by the DMA 300 are discharged to the outside of the measuring system 1.

The aerosol particle measuring device 400 measures the number of the aerosol particles classified out by the DMA 300. The measuring device 400 includes at least one of a Faraday cup aerosol electrometer (hereinafter, referred to as FCAE) 401 and a condensation particle counter (hereinafter, referred to as CPC) 501, The FCAE 401 catches the charged aerosol particles classified out by the DMA 300 and measures a current value corresponding to the number of charges on the caught particles. Further, with the aerosol particles classified out by the DMA 300 being condensation nuclei, the CPC 501 condenses alcohol or water to grow them into large droplets, and optically detects the enlarged droplets to measure the number of the particles. The concrete contents regarding the aerosol particles measured by the FCAE 401 and the CPC 501 will be further described later with reference to another drawing.

A result of the measurement by the aerosol particle measuring device 400 is transmitted to the measurement result analyzing device 600.

The measurement result analyzing device 600 counts the number of the aerosol particles with respect to each particle size based on the data measured by the FCAE 401 or the CPC 501. A concrete counting method will be further described later with reference to another drawing. Information on the number of the aerosol particles counted by the measurement result analyzing device 600 is transmitted to the counting result outputting device 700.

Regarding the number of the aerosol particles counted by the measurement result analyzing device 600, the counting result outputting device 700 displays the number of the particles with respect to each particle size.

[Aerosol Particles in Atmosphere]

Next, the aerosol particles in the atmosphere collected by the aerosol particle collecting device 100 will be described.

Figure 2:
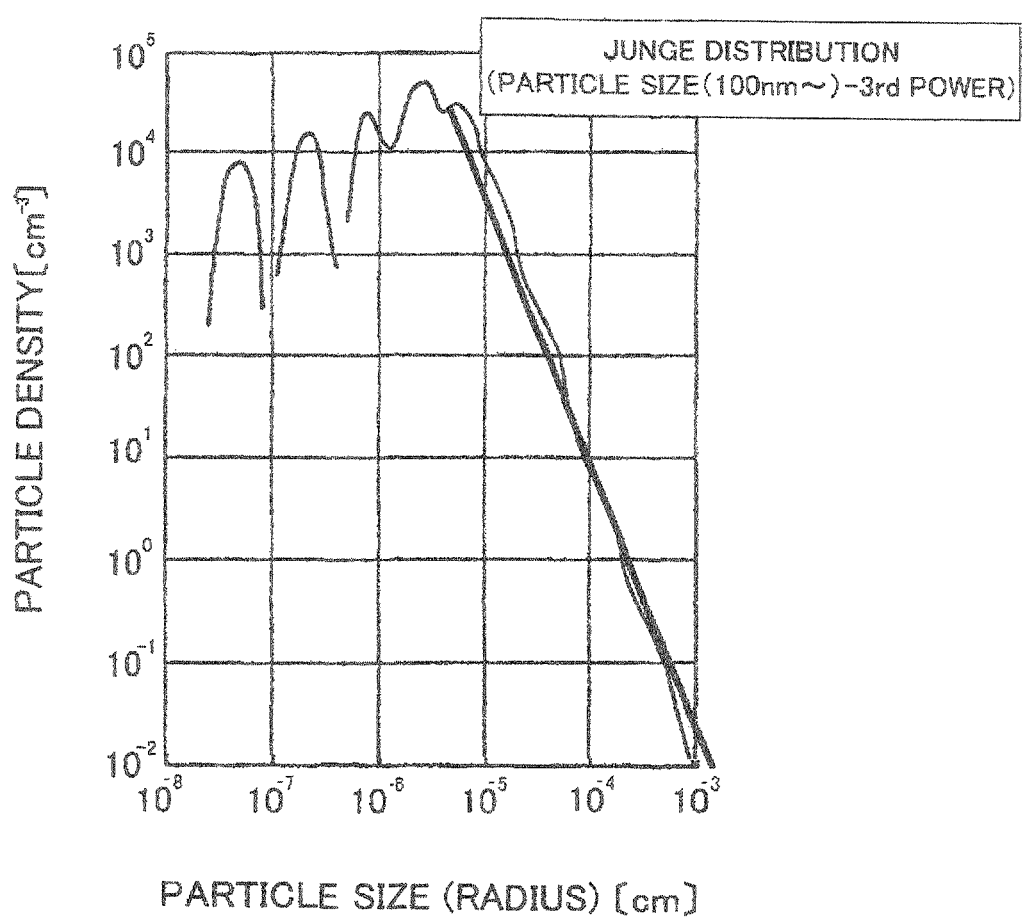
FIG. 2 is an explanatory chart of an aerosol particle density distribution (Junge distribution) in the atmosphere.

FIG. 2 is an explanatory chart of aerosol particle density distribution in the atmosphere (Junge distribution (1952)) (Reference: H Israel, Atmospheric Electricity, Volume 1, pp. 153, 1970).

As shown in FIG. 2, as for the aerosol particles in the atmosphere, the particle density distribution thereof differs depending on particle size, and concretely, the density with respect to each particle size follows the Junge distribution. According to the Junge distribution, it is shown that the distribution of the aerosol particles whose particle size is larger than 100 nm is based on an inverse cubic size distribution law, and aerosol particles with a larger particles size are less suspended in the atmosphere. For example, the number of suspended aerosol particles smaller than 100 nm is approximately several ten thousands per cubic cm, while the number of suspended aerosol particles larger than 100 nm is only several per cubic cm. That is, the Junge distribution shows that compared with the number of aerosol particles with a 100 nm particle size (in FIG. 2, a 50 nm radius), the number of aerosol particles with a 200 nm particle size (in FIG. 2, a 100 nm radius) is approximately one tenth, and the number of aerosol particles with a 300 nm particle size (in FIG. 2, a 150 nm radius) is approximately one thirtieth, and the number of larger aerosol particles is very small based on the inverse cubic size distribution law.

Therefore, it is understood that, based on the Junge distribution shown in FIG. 2, most of the aerosol particles in the atmosphere collected by the aerosol particle collecting device 100 are aerosol particles with 100 nm or less, and the number of aerosol particles with 100 nm or more is extremely small based on the inverse cubic size distribution law. Further, aerosol particles with 200 nm or more and aerosol particles with 300 nm or more are not suspended in the atmosphere almost at all, and accordingly, are not collected almost at all by the aerosol particle collecting device 100. These also apply to the aerosol particles generated by the aerosol particle generating device 100.

[Neutralizer]

Next, it will be described that the collected or generated aerosol particles are charged by the neutralizer 200.

Figure 3:
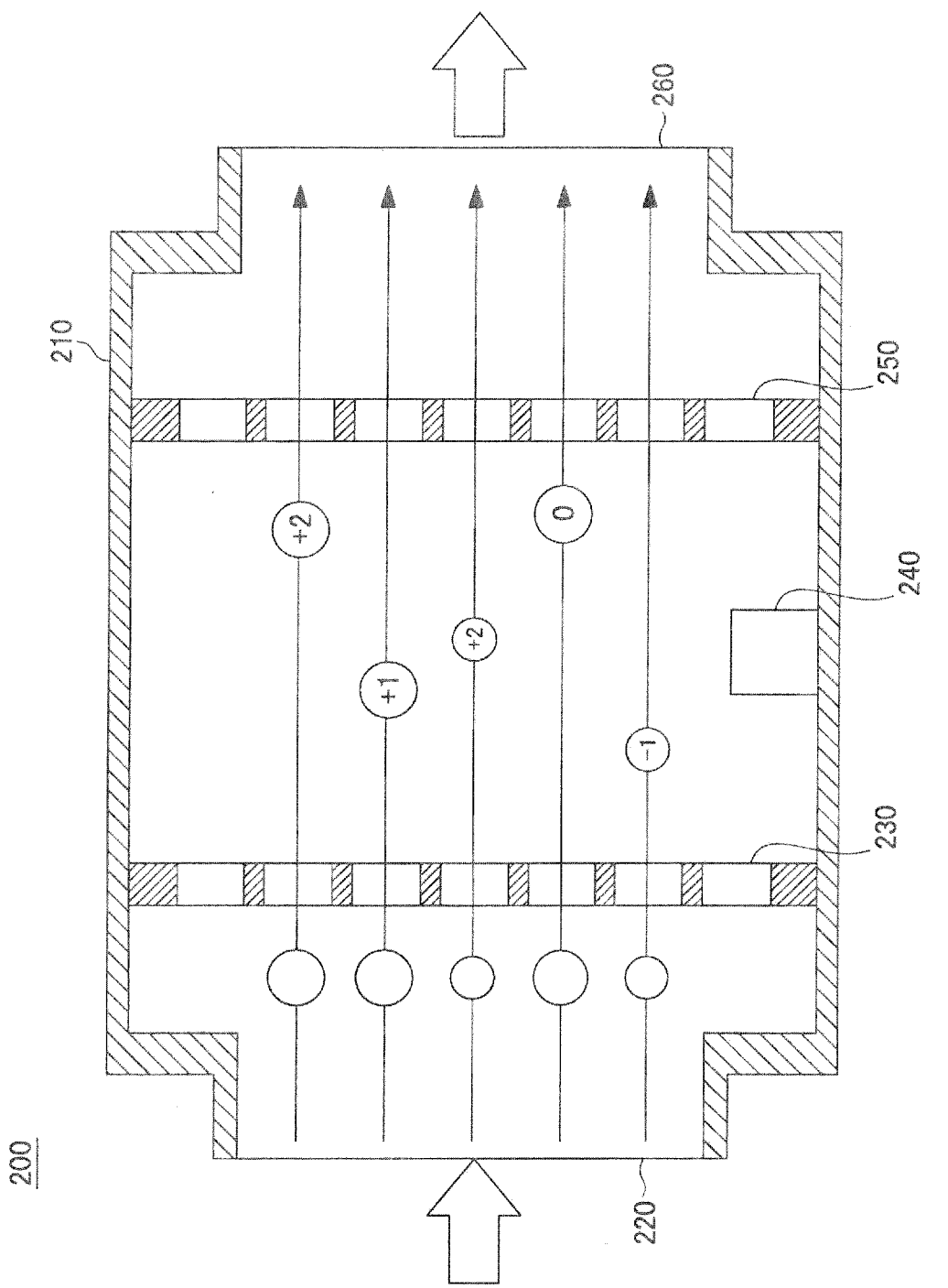
FIG. 3 is an explanatory diagram of a neutralizer.

As shown in FIG. 3, the neutralizer 200 lets the aerosol particles flow thereinto from an inflow port 220 provided in its vessel 210. The vessel 210 is formed of, for example, a SUS vessel. Further, in the vessel 210, a pair of porous plates 230, 250 is provided, for instance, and a radioactive source 240 is installed in a region between the porous plates 230, 250. As the radioactive source 240, a $^{241}$AM, $^{85}$Kr, $^{210}$Po, or the like is used. Installing the radioactive source 240 maintains the charged equilibrium state in the region between the porous plates 230, 250, and the aerosol particles are charged when passing in the region. Next, a charging probability of the aerosol particles which differs depending on each particle size will be described.

[Charging Probability Distribution]

Figure 4:
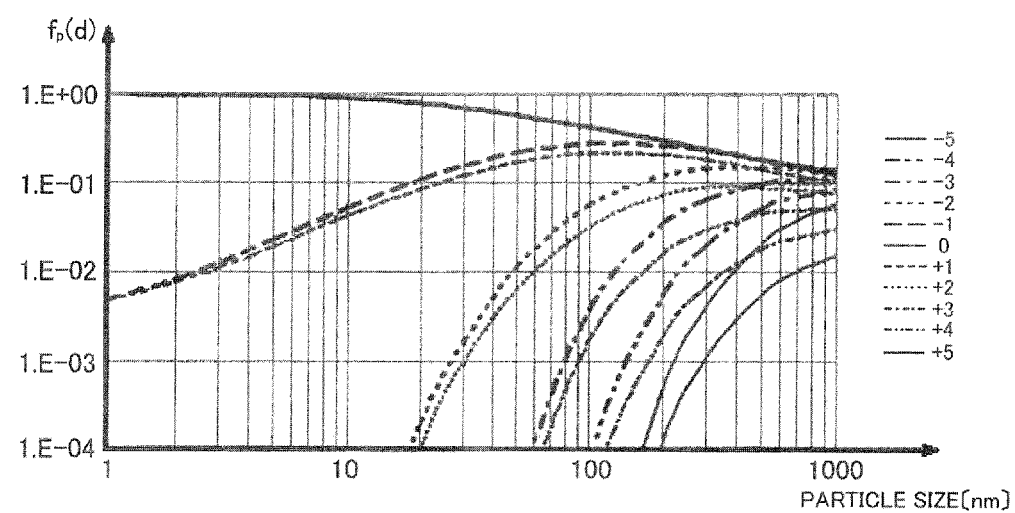
FIG. 4 is an explanatory chart of a charging probability distribution.

FIG. 4 is an explanatory chart of a charging probability distribution (ISOO15900:2009).

FIG. 4 shows charging probabilities for aerosol particles to have a charge of zero to a charged of ±5 at the charged equilibrium state. The smaller the particle size is, the less likely aerosol particles are charged, and on the contrary, the larger the particle size is, the more likely aerosol particles are charged, and further the more likely they are multiply charged.

For example, approximately 98% of aerosol particles with a 1 nm particle size are not charged and approximately another 1% and the other 1% are charged to have a charge of −1 and a charge of +1 respectively. Besides, approximately 90% or more of aerosol particles with a particle size of up to 10 nm are not charged.

For example, among aerosol particles with a 100 nm particle size, approximately 40% are not charged, approximately 30% are charged to have a charge of −1, approximately 20% are charged to have a charge of +1, approximately 6% are charged to have a charge of −2, and approximately 3% are charged to have a charge of +2. Further, among aerosol particles with a 200 nm particle size, approximately 30% are not charged, approximately 30% are charged to have a charge of −1, approximately 20% are charged to have a charge of +1, approximately 12% are charged to have a charge of −2, approximately 8% are charged to have a charge of +2, approximately 3% are charged to have a charge of −3, and approximately 2% are charged to have a charge of +3, Further, among aerosol particles with a 300 nm particle size, approximately 20% are not charged, approximately 20% are charged to have a charge of −1, approximately 15% are charged to have a charge of +1, approximately 9% are charged to have a charge of −2, approximately 7% are charged to have a charge of +2, approximately 3% are charged to have a charge of −3, and approximately 2% are charged to have a charge of +3, and approximately 2% are charged to have a charge of −4.

Next, it will be described that the aerosol particles charged by the neutralizer 200 are classified by the DMA 300 will be described.

[Differential Mobility Analyzer: DMA]

Figure 5:
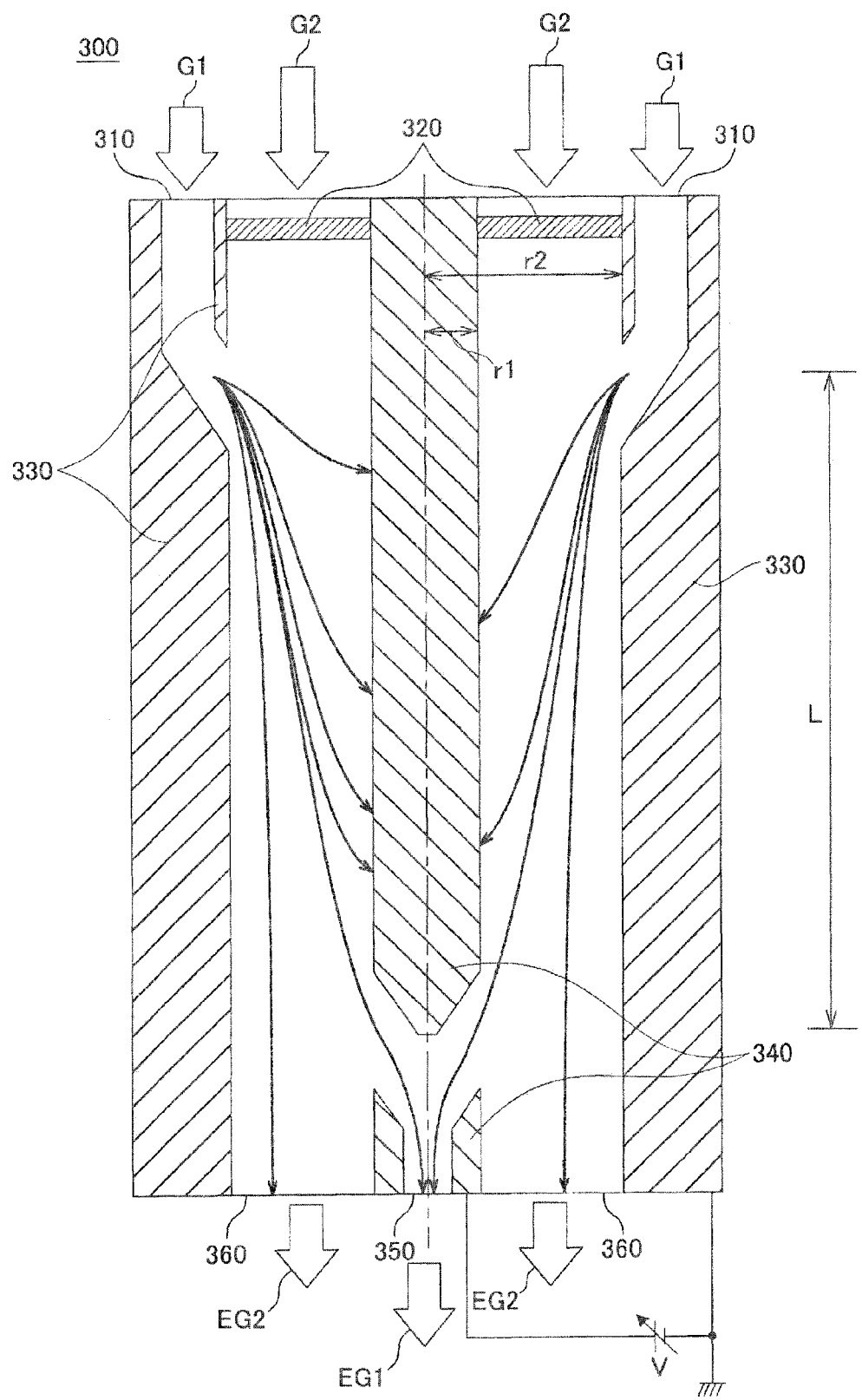
FIG. 5 is an explanatory diagram of a DMA.

As shown in FIG. 5, the DMA 300 has a dual cylindrical shape composed of an inner cylinder and an outer cylinder. The atmosphere (sample gas G1) containing the aerosol particles charged by the neutralizer 200 is made to flow with clean air (sheath gas G2). Note that a filter 320 is provided at a position preceding a position where the sheath gas G2 joins the aerosol particles, and impurities in the sheath gas G2 are removed by the filter 320.

The outer cylinder of the DMA 300 is used as an outer electrode 330 and the inner cylinder of the DMA 300 is used as an inner electrode 340. The outer electrode 330 is installed apart from a center axis of the DMA 300 by a distance $r_2$, and the inner electrode 340 is installed apart from the center axis of the DMA 300 by a distance $r_1$. A voltage V is supplied between the outer electrode 330 and the inner electrode 340. Therefore, the sample gas G1 containing the aerosol particles which flows in from the inflow port 310 flows with the sheath gas G2 in an electric field to which the voltage V is supplied.

An electrostatic force and a resistance force act on the aerosol particles moving in the sheath gas. Further, as for particles moving in a fluid while receiving an electrostatic attraction force, since the electrostatic force and the resistance force are balanced in a steady state, a constant velocity v of the particles is proportional to an electric field E, and a relation of v=ZE holds, where Z is electrical mobility.

Here, the electrical mobility Z is expressed by the following mathematical expression (1).

$$Z(d, p) = \frac{p \cdot e}{3\pi \mu_g d} \left\{ 1 + \frac{2l_g}{d}\left[ 1.165 + 0.483\exp\left(-\frac{0.997d}{2l_g}\right) \right] \right\} \quad (1)$$

In the mathematical expression (1) expressing the electrical mobility Z, p represents the number of charges on the aerosol particles, e represents the elementary charge, $\mu_g$ represents the dynamic viscosity of a gas (particle size of a gas), d represents the particle diameter particle size of the aerosol particles, and l g represents a mean free path of gas molecule.

Therefore, the charged aerosol particles flowing into the DMA 300 from its inflow port 310 move along the trajectories shown in FIG. 5 based on the electrical mobility Z. Concretely, aerosol particles with large particle sizes whose number of charges is 2 and 3 also reach an exit port 350 for classified particle together with aerosol particles with small particle sizes whose number of charges is 1 (EG1). As described above, the DMA 300 is capable of classifying out the aerosol particles based on each given electrical mobility, and classifies out not only singly charged particles but also multiply charged particles. Incidentally, the aerosol particles not classified out are discharged from an exit port 360 (EG2).

Further, the electrical mobility Z can also be derived from the structure of the DMA 300 (the radius r1 of the inner electrode, the radius $r_2$ of the outer electrode, and a distance L up to the classifying) and set items regarding the operation of the DMA 300, and is expressed by the following mathematical expression (2) when a flow rate $q_2$ of the sample gas is equal to its discharge rate $q_3$ from the exit port 350 for classified particle and a flow rate $q_1$ of the sheath gas is equal to its discharge rate $q_4$ from the exit port 360 ($q_1=q_4$, $q_2=q_3$).

$$Z_1(U) = \frac{q_1 \cdot ln(r_2/r_1)}{2\pi \cdot L} \cdot \frac{1}{U} = A \cdot \frac{1}{U} \quad (2)$$

In the mathematical expression (2) expressing the electrical mobility Z, U represents a supplied voltage.

Therefore, the electrical mobility Z can be adjusted by the supplied voltage U if the flow rate $q_1$ of the sheath gas is constant. Note that the flow rate $q_2$ of the sample gas÷ the flow rate $q_1$ of the sheath gas is called a ratio of flow rate.

[Aerosol Particles Corresponding to Electrical Mobility]

Figure 6:
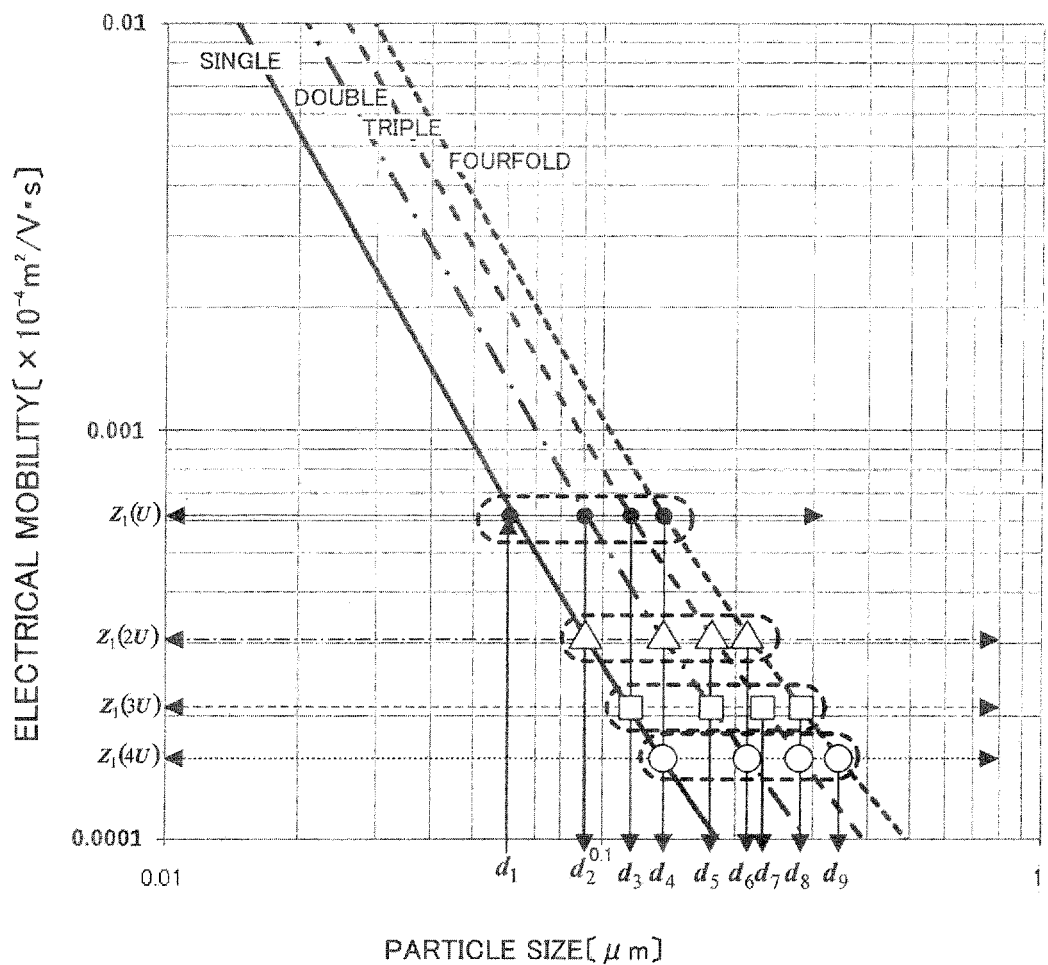
FIG. 6 is an explanatory chart of particle size and number of charges of aerosol particles that are classified out, corresponding to electrical mobility.

FIG. 6 shows an example of the electrical mobility which is found from the mathematical expression (1) and the mathematical expression (2) expressing the electrical mobility Z, in relation to the particle size, when the DMA 300 is operated. Here, the numbers of charges up to 4 are shown, and in observing the particle size distribution, there is almost no problem if the consideration is given up to approximately 4 charges.

For example, the aerosol particles classified out based on the electrical mobility Z(U) when the voltage U is supplied to the DMA 300 are represented by the four black dots (●) depicted in FIG. 6. They are not only aerosol particles with a particle size $d_1$ whose number of charges is 1, but also aerosol particles with a particle size $d_2$ whose number of charges is 2, and aerosol particles with a particle size $d_3$ whose number of charges is 3, and aerosol particles with a particle size $d_4$ whose number of charges is 4. Here, the particle size $d_1$ is approximately 60 nm, the particle size $d_2$ is approximately 90 nm, the particle size $d_3$ is approximately 115 nm, and the particle size $d_4$ is approximately 135 nm.

Next, electrical mobility when a voltage 2U twice as high as that for the aforesaid electrical mobility Z(U) is supplied to the DMA 300 in order to classify out the aerosol particles with the particle size $d_2$ and with the number of charges of 2 which are classified out based on the electrical mobility Z(U) is defined as Z(2U). The aerosol particles classified out by the DMA 300 at this time are represented by the four triangular marks (Δ) depicted in FIG. 6. They are aerosol particles with the particle size $d_2$ whose number of charges is 1, aerosol particles with the particle size $d_4$ whose number of charges is 2, aerosol particles with a particle size $d_5$ whose number of charges is 3, and aerosol particles with the particle size $d_6$ whose number of charges is 4. As for the aerosol particles whose number of charges is 2, those with the same particle size as that of the aerosol particles with the number of charges of 4 classified out based on the electrical mobility Z(U) are classified out. Note that the other particle size $d_5$ is approximately 180 nm and the other particle size $d_6$ is approximately 210 nm.

Thereafter, similarly, aerosol particles classified out based on electrical mobility Z(3U) when a voltage 3U three times as high as the voltage for the electrical mobility Z(U) is supplied to the DMA 300 are represented by the four square marks (□) depicted in FIG. 6, and aerosol particles with the same particle size $d_3$ as that of the aerosol particles with the number of charges of 3 classified out based on the electrical mobility Z(U) are classified out, and aerosol particles with the same particle size $d_5$ as that of the aerosol particles with the number of charges of 3 classified out based on the electrical mobility Z(2U) are classified out. Further, aerosol particles classified out based on electrical mobility Z(4U) when a voltage 4U four times as high as the voltage for the electrical mobility Z(U) is supplied to the DMA 300 are represented by the four white circular marks (○) depicted in FIG. 6, and aerosol particles with the same particle size $d_4$ as that of the aerosol particles with the number of charges of 4 classified out based on the electrical mobility Z(U) are classified out, and aerosol particles with the same particle size $d_6$ as that of the aerosol particles with the number of charges of 4 classified out based on the electrical mobility Z(2U) are classified out, and aerosol particles with the same particle size $d_8$ as that of the aerosol particles with the number of charges of 4 classified out based on the electrical mobility Z(3U) are classified out. Note that the particle size $d_7$ is approximately 240 nm, the particle size $d_8$ is approximately 290 nm, and the particle size $d_9$ is approximately 340 nm.

The aerosol particles classified out by the DMA 300 based on the electrical mobility Z are next sent to the aerosol particle measuring device 400, where the data regarding the number of the aerosol particles are measured. Hereinafter, the FCAE 401 will be first described, and next the CPC 501 will be described.

[Faraday Cup Aerosol Electrometer: FCAE]

Figure 7:
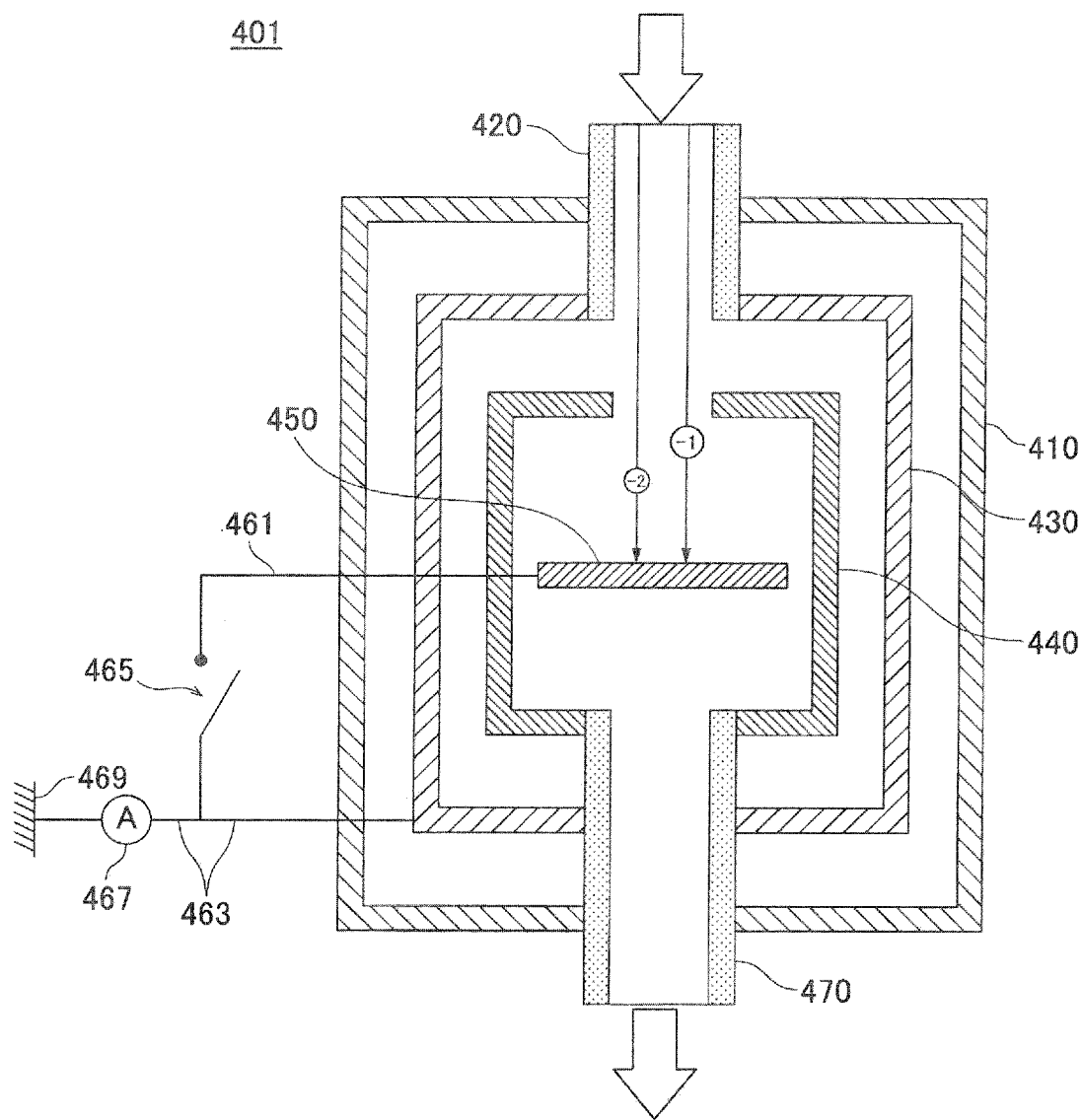
FIG. 7 is an explanatory diagram of a FCAE.

As shown in FIG. 7, the FCAE 401 lets the aerosol particles classified out by the DMA 300 flow thereinto from an inflow port 420 provided in its vessel 410. In the vessel 410, a conductive materials 430 is installed, and an insulator 440 is installed in the conductive materials 430. Further, in the insulator 440, an aerosol particle collector 450 is installed, and this collector 450 is made of a conductive materials collecting (catching) the charged aerosol particles. The aerosol particle collector 450 and the conductive materials 430 are insulated from each other by the insulator 440. Further, the conductive materials 430 and a ground 469 are connected by a lead wire 463, and an ammeter 467 is installed on the lead wire 463. Further, one end of a lead wire 461 is connected to the aerosol particle collector 450, and the other end of the lead wire 461 is connected to the ground 469 via a switch 465.

With the above-described structure, when the charged aerosol particles flow into the FCAE 401, they are collected by the aerosol particle collector 450, so that electric charges are accumulated in the aerosol particle collector 450. Then, when the switch 465 is set to ON (is energized), the electric charges accumulated in the aerosol particle collector 450 move as a unit, and the ammeter 467 is capable of measuring a current equivalent to the total number of the electric charges. The calculation of the number of the aerosol particles will be further described later with reference to another drawing.

[Condensation Particle Counter (CPC)]

Next, the CPC 501 will be described.

Figure 8:
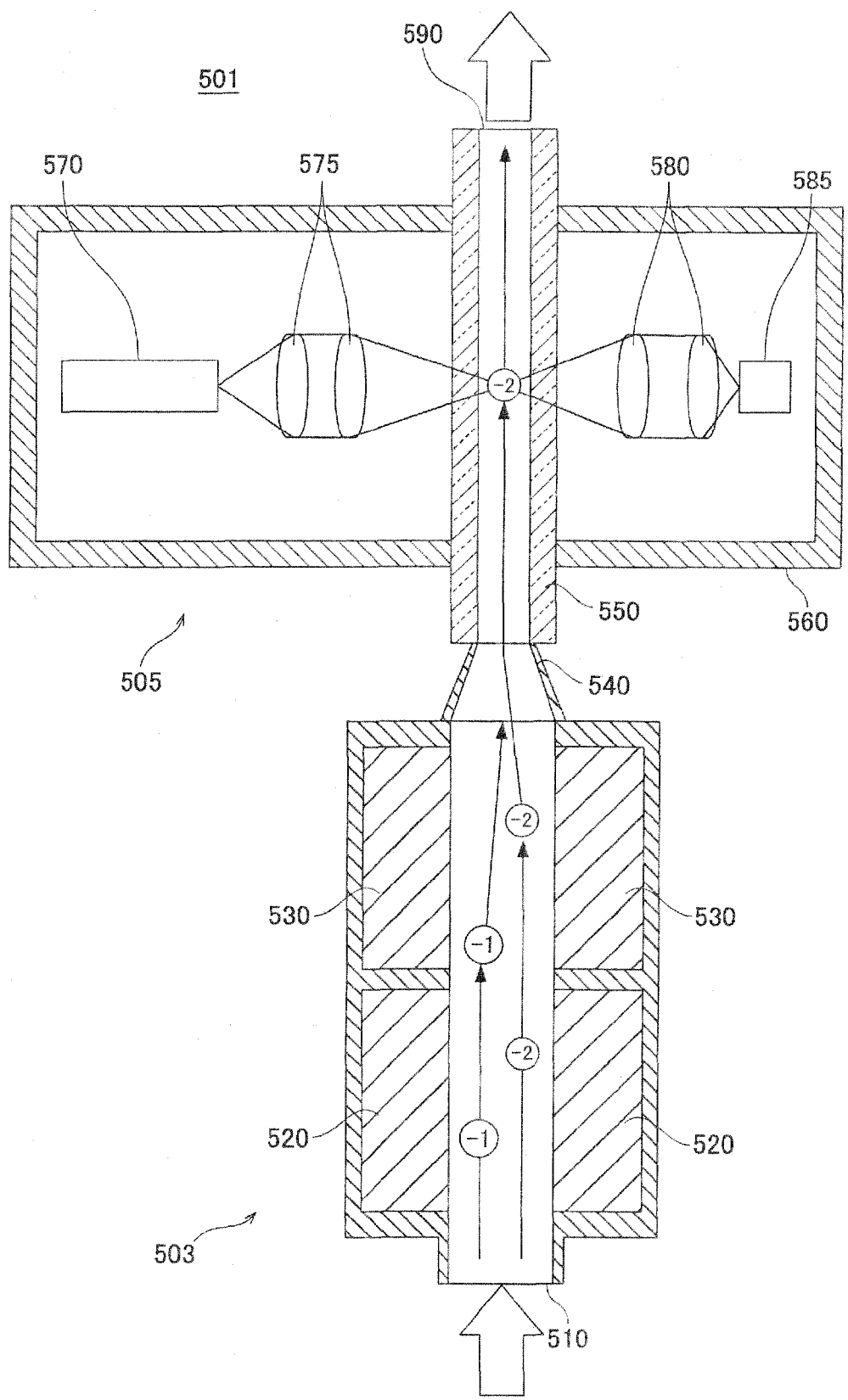
FIG. 8 is an explanatory diagram of a CPC.

As shown in FIG. 8, the CPC 501 includes: an aerosol particle condenser 503 which grows the aerosol particles large by condensation; and an aerosol particle optical detector 505 which detects the grown aerosol particles by an optical system.

The aerosol particles classified out and sent by the DMA 300 are made to flow into the aerosol particle condenser 503 from its inflow port 510. The aerosol particle condenser 503 is composed of a saturation part 520 and a condensing part 530. In the saturation part 520, alcohol or distilled water is diffused in a vapor form by being heated. Further, in the condensing part 530, gas that passes therein is cooled. Therefore, the aerosol particles flowing into the aerosol particle condenser 503 join the alcohol vapor or the water vapor in the saturation part 520 and both of them are sent to the condensing part 530. Then, in the condensing part 530, the condensation occurs with the aerosol particles serving as condensation nuclei, and they grow into large droplets owing to the alcohol vapor or the water vapor. The aerosol particles which are turned into the large droplets by the aerosol particle condenser 503 are sent to the aerosol particle optical detector 505 via a connection passage 540.

The aerosol particle optical detector 505 includes a flow cell 550, a light shielding vessel 560, a light emitting device 570, an irradiation optical lens system 575, a light-condensing optical lens system 580, and a light receiving device 585. The flow cell 550 is installed to penetrate through the light shielding vessel 560. Further, the light emitting device 570, the irradiation optical lens system 575, the light-condensing optical lens system 580, and the light receiving device 585 are installed in the light shielding vessel 560, and the light shielding vessel 560 has a structure so as not to allow light to enter its interior from the outside.

When scattered lights (reflected lights) from the aerosol particles flowing in the flow cell 550 are received, the aerosol particles are detected.

In the measurement of the aerosol particles classified out by the DMA 300, the FCAE 401 outputs, as a current, an accumulation value of the numbers of charges on the aerosol particles classified out per predetermined time. Further, the CPC 501 outputs a result equivalent to the number of the aerosol particles. Information on the result that is output is next transmitted to the measurement result analyzing device 600.

[Measurement Result Analyzing Device]

Next, in the measurement result analyzing device 600, the number of the aerosol particles is counted with respect to each particle size, based on the data measured by the FCAE 401 or the CPC 501. The measurement result analyzing device 600 includes an arithmetic operating function and a memory function, the process contents of the arithmetic operation are recorded in the memory function in advance, and the arithmetic operating function reads the process contents of its arithmetic operation as required, thereby counting the number of the aerosol particles with respect to each particle size from the data measured by the FCAE 401 or the CPC 501.

[Counting Result Outputting Device]

The counting result outputting device 700 displays the result of the counting of the aerosol particles, with respect to each particle size. For example, a display device (not shown) includes a display part for "Size (nm)" indicating a reference of the size of the aerosol particles and a display part for "Count" indicating the number (count value) of the counted aerosol particles corresponding to each particle size. The display part for "Size (nm)" displays a value of the reference particle size. The display part for "Count" displays the total number of the particles found from charging probability distribution, the number of particles with the reference particle size whose number of charges is 1, and the like. Further, they may be displayed as graphs. A display manner may be any as desired and is not limited to the example described here.

Incidentally, the counting result outputting device 700 may further include an external output terminal and may output data to another device through the terminal.

[Measurement of Aerosol Particles in Atmosphere]

In the measurement of the aerosol particles in the atmosphere, it is assumed that the aerosol particles whose particle size is larger than 100 nm are suspended in the atmosphere based on the inverse cubic size distribution law (hinge distribution), which is described when the particle density of the aerosol particles in the atmosphere is described by using FIG. 2.

Figure 10:
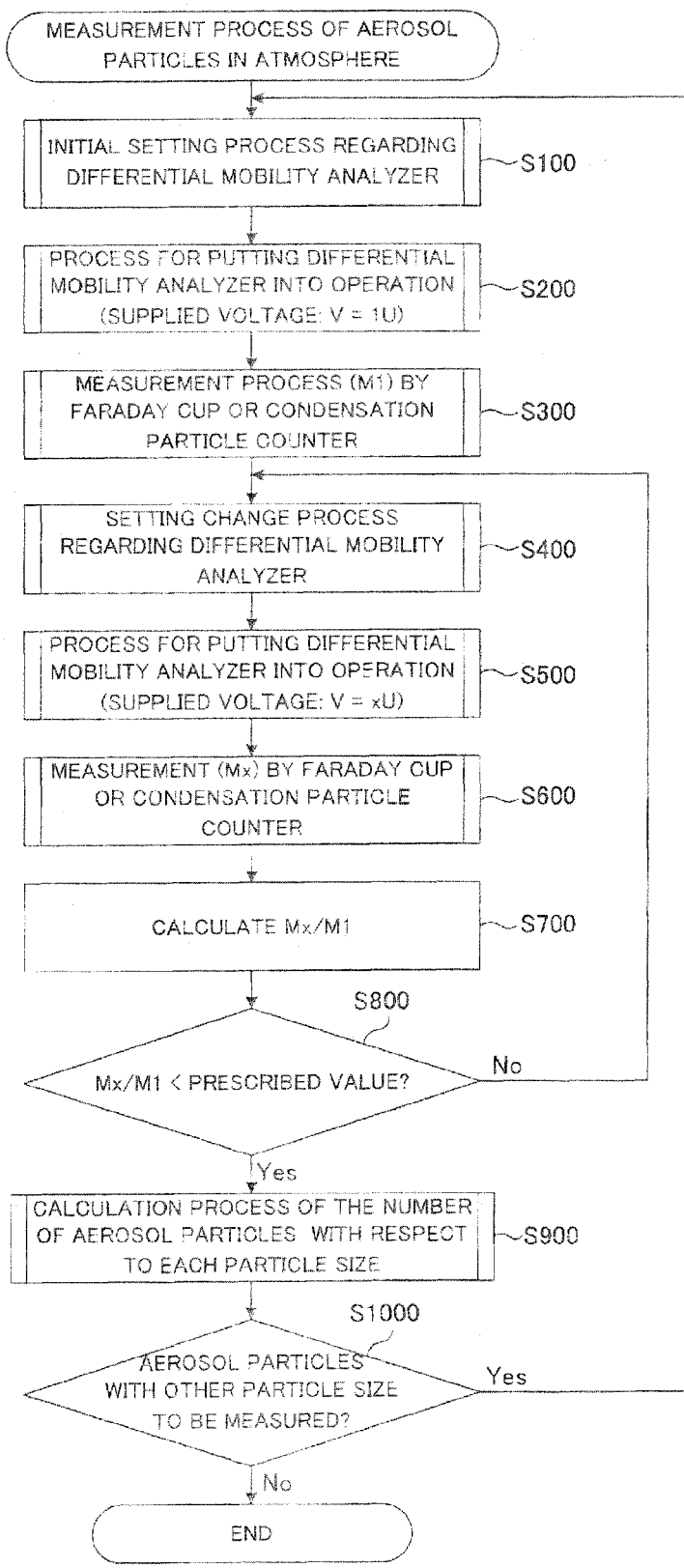
FIG. 10 is a flowchart showing a procedure example of a measurement process of the aerosol particles in the atmosphere.

FIG. 10 is a flowchart showing a measurement procedure of the aerosol particles in the atmosphere. Hereinafter, the contents will be described along the procedure example. Incidentally, the process in FIG. 10 may be executed by a control unit built in the particle size distribution measuring system 1.

Step S100: First, the particle size distribution measuring system 1 executes an initial setting process regarding the DMA 300. The concrete contents of the process will be further described later with reference to another flowchart.

[Initial Setting Process regarding DMA]

Figure 11:
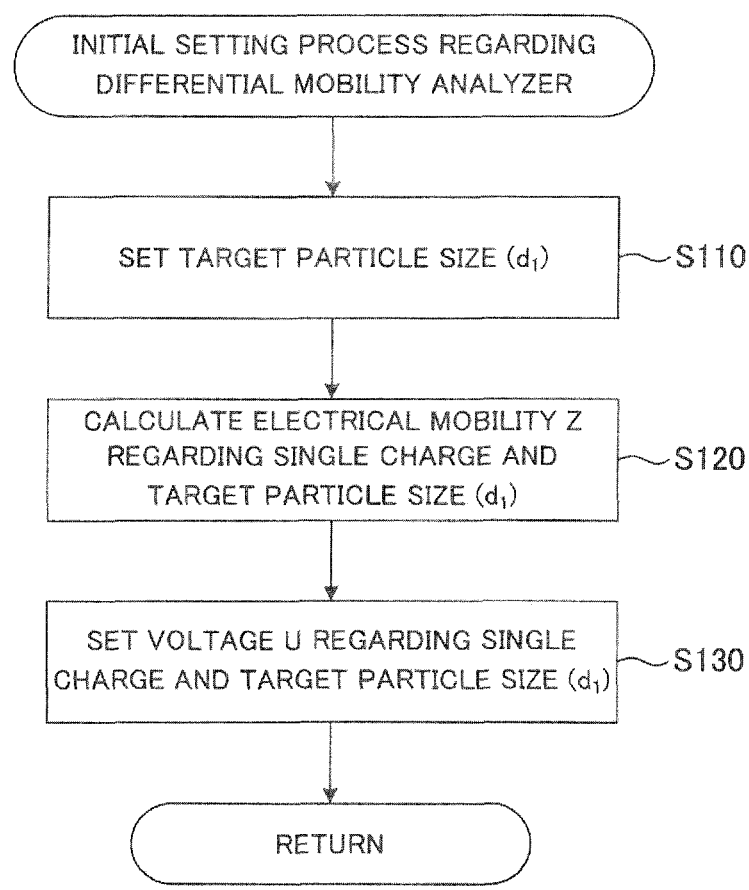
FIG. 11 is a flowchart showing a procedure example of an initial setting process regarding the DMA.

FIG. 11 is a flowchart showing a procedure example of the initial setting process regarding the DMA 300. Incidentally, the process in FIG. 11 may be executed by the control unit built in the particle size distribution measuring system 1.

Step S110: The particle size distribution measuring system 1 sets the particle size ($d_1$) as a measurement target. Concretely, the particle size distribution measuring system 1 sets the particle size ($d_1$) of the aerosol particles that are to be classified out by the DMA 300, on assumption that they are singly charged. The particle size distribution measuring system 1 next executes Step S120.

Step S120: The particle size distribution measuring system 1 executes the calculation of the electrical mobility 7 regarding the target particle size ($d_1$) of the singly charged particles. Concretely, the particle size distribution measuring system 1 executes the calculation of the electrical mobility 7 by using the above-described mathematical expression (1). The particle size distribution measuring system 1 next executes Step S130.

Step S130: The particle size distribution measuring system 1 sets the voltage U that is to be supplied to the DMA 300, as a voltage necessary for classifying out the singly charged aerosol particles with the target particle size ($d_1$). Concretely, particle size distribution measuring system 1 calculates the voltage U that is to be supplied to the DMA 300, by using the electrical mobility Z calculated in the previous process Step S120 and the above-described mathematical expression (2).

Upon finishing the above-described procedure, the particle size distribution measuring system 1 returns to the measurement process (FIG. 10) of the aerosol particles in the atmosphere.

Step S200: Next, the particle size distribution measuring system 1 executes a process for putting the DMA 300 into operation. Concretely, the particle size distribution measuring system 1 supplied the voltage U calculated in the previous process Step S130 to the DMA 300 (supplied voltage V=1U) to put the DMA 300 into operation and classifies out the aerosol particles based on the electrical mobility $Z_1(U)$. The particle size distribution measuring system 1 next executes Step S300.

Step S300: The particle size distribution measuring system 1 executes the measurement (M1) by the FCAE 401 or the CPC 501. Here, the M1 represents the measurement result of the aerosol particles classified out based on the electrical mobility $Z_1(U)$. When the FCAE 401 or the CPC 501 finishes the measurement of the aerosol particles classified out based on the electrical mobility $Z_1(U)$, the particle size distribution measuring system 1 next executes Step S400.

Step S400: The particle size distribution measuring system 1 executes a setting change process regarding the DMA 300. The concrete contents of the process will be further described later with reference to another flowchart.

[Setting Change Process regarding DMA]

Figure 12:
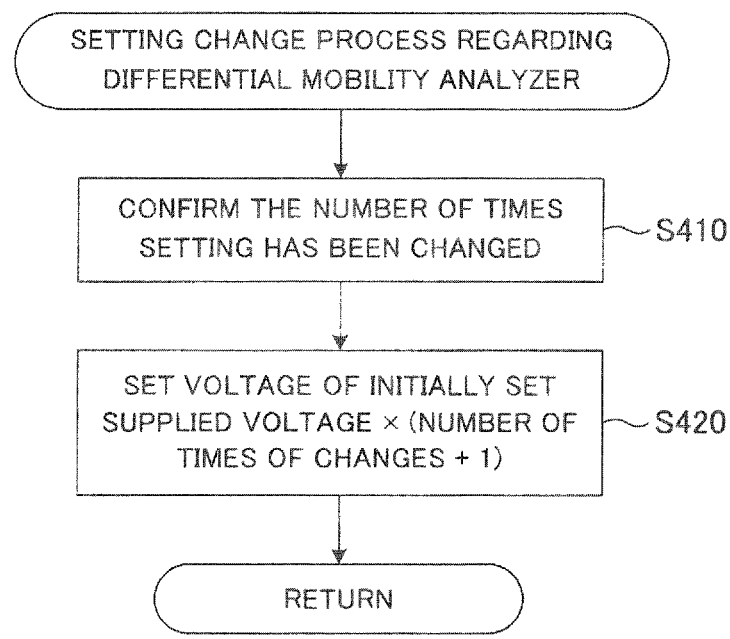
FIG. 12 is a flowchart showing a procedure example of a setting change process regarding the DMA.

FIG. 12 is a flowchart showing a procedure example of the setting change process regarding the DMA 300. Hereinafter, the contents will be described along the procedure example. Incidentally, the process in FIG. 12 may be executed by the control unit built in the particle size distribution measuring system 1.

Step S410: The s particle size distribution measuring system 1 confirms the number of times the setting has been changed. Concretely, the particle size distribution measuring system 1 confirms the number of times the voltage V supplied to the DMA 300 has been changed. For example, when the voltage V set in the previous process is the initially set U, the number of times the setting has been changed corresponds to 1 indicating the first time. Besides, when the voltage V set in the previous process is 2U indicating the second time (or 3U indicating the third time), the number of times the setting has been changed is 2 (or 3) indicating the second time (or the third time). The particle size distribution measuring system 1 next executes Step S420.

Step S420: The particle size distribution measuring system 1 executes the setting for supplied the initially set supplied voltage (U)×(the number of times of the changes+ 1). For example, when the number of times of the changes confirmed in the previous process Step S410 is 1, the particle size distribution measuring system 1 sets the voltage that is to be supplied to the DMA 300 to 2U. Besides, when the number of times of the changes is 2 (or 3), the particle size distribution measuring system 1 sets the voltage that is to is be supplied to the DMA 300 to 3U (or 4U).

Upon finishing the above-described procedure, the particle size distribution measuring system 1 returns to the measurement process (FIG. 10) of the aerosol particles in the atmosphere.

Step S500: The particle size distribution measuring system 1 executes a process for putting the DMA 300 into operation. Concretely, the particle size distribution measuring system 1 supplies the voltage 2U (or 3U, 4U) set in the previous process Step S420 to the DMA 300 (supplied voltage V=2U (or 3U, 4U)) to put the DMA 300 into operation and classifies out the aerosol particles based on the electrical mobility $Z_1(2U)$ (or $Z_1(3U)$, $Z_1(4U)$). The particle size distribution measuring system 1 next executes Step S600.

Step S600: The particle size distribution measuring system 1 executes a measurement Mx by the FCAE 401 or the CPC 501. The FCAE 401 or the CPC 501 outputs a measurement result Mx. Here, x represents any one of 2 to 4, M2 represents the measurement result of the aerosol particles classified out based on the electrical mobility $Z_1(2U)$, M3 represents the measurement result of the aerosol particles classified out based on the electrical mobility $Z_1(3U)$, and M4 represents the measurement result of the aerosol particles classified out based on the electrical mobility $Z_1(4U)$. When the measurement by the FCAE 401 is finished, the particle size distribution measuring system 1 next executes Step S700.

Step S700: From the measurement result M1 at the time of the initial setting and the measurement result Mx obtained when the setting is changed, the particle size distribution measuring system 1 calculates Mx/M1 being a ratio therebetween. Concretely, the particle size distribution measuring system 1 refers to the measurement result M1 obtained when, in the previous Step S300, the FCAE 401 or the CPC 501 measures the aerosol particles classified out based on the electrical mobility $Z_1(U)$. Further, the particle size distribution measuring system 1 refers to the measurement result M2 (or M3, M4) obtained when, in the previous process step S600, the FCAE 401 measures the aerosol particles classified out based on the electrical mobility $Z_1(2U)$ (or $Z_1(3U)$, $Z_1(4U)$). Then the particle size distribution measuring system 1 calculates Mx/M1. It is possible to calculate Mx/M1 by using the measurement result analyzing device 600.

Step S800: The particle size distribution measuring system 1 confirms whether or not re-measurement is required. It is possible to confirm this by using the measurement result analyzing device 600. Concretely, based on Mx/M1 calculated in the previous Step S700, the particle size distribution measuring system 1 confirms whether or not it is smaller than a prescribed value (for example, 0.01:1%). If the prescribed value is set as approximately 1%, even disregarding the value of Mx/M1 causes no problem in observing the particle size distribution. It should be noted that the prescribed value is not limited to 1% and may be 0.1% and is appropriately adjustable. When confirming that Mx/M1 is smaller than the prescribed value (Yes), the particle size distribution measuring system 1 next executes Step S900. On the other hand, when Mx/M1 is not smaller than the prescribed value (No), the particle size distribution measuring system 1 next executes Step S400.

Step S900: The particle size distribution measuring system 1 calculates the number of the aerosol particles ($d_1$) classified out by the DMA 300. It is possible to calculate this by using the measurement result analyzing device 600. Here, a description will be given of a case where M2/M1 and M3/M1 are not smaller than the prescribed value (1%) and M4/M1 is smaller than the prescribed value (1%). A description of other cases will be skipped because the calculation is possible as required based on the calculation method using the following mathematical expressions.

Note that the measurement results M1, M2, M3, M4 measured by the FCAE 401 are current-equivalent and $M_{FCAE}(Z_1(U))$ is quantity-equivalent. On the other hand, the measurement results M1, M2, M3, M4 measured by the CPC 501 are quantity-equivalent and $M_{CPC}(Z_1(U))$ is similarly quantity-equivalent.

Here, a distribution function of the charged aerosols particles corresponding to each particle size, actually classified out by the DMA 300 based on the electrical mobility $Z_1(U)$ is defined as follows. The distribution function of singly charged aerosol particles corresponding to the particle size $d_1$ is defined as $C_1(Z_1(U))$, the distribution function of doubly charged aerosol particles corresponding to the particle size $d_2$ is defined as $C_2(Z_1(U))$, the distribution function of triply charged aerosol particles corresponding to the particle size $d_3$ is defined as $C_3(Z_1(U))$, and the distribution function of fourfold charged aerosol particles corresponding to the particle size $d_4$ is defined as $C_4(Z_1(U))$. Note that the distribution function expresses the quantity of the relevant particles. For example, $C_1(Z_1(U))$ expresses the quantity of the singly charged particles corresponding to the electrical mobility $Z_1(U)$.

Therefore, the measurement result measured by the FCAE 401 or the CPC 501 is expressed by the following mathematical expression (3) or mathematical expression (4) when the aforesaid distribution function of the aerosol particles is used.

$$M_{FCAE}(Z_1(U)) = \eta_{FCAE}(Z_1(U)) \cdot \sum_{p=1}^{4} p \cdot C_p(Z_1(U)) \qquad (3)$$

Here, $M_{FCAE}(Z_1(U))$ represents the quantity obtained from the measurement result by the FCAE 401 for the aerosol particles classified out based on $Z_1(U)$, $\eta_{FCAE}(Z_1(U))$ represents detection efficiency of the FCAE 401 for the aerosol particles classified out based on $Z_1(U)$, and p represents the number of charges. Note that $\eta_{FCAE}(Z_1(U))$ is generally 1 (concretely, 0.99999), Further, detection efficiency is also 1 in the other $\eta_{FCAE}Z_1(2U)$, $\eta_{FCAE}Z_1(3U), \ldots \eta_{FCAE}Z_1(pU)$.

$$M_{CPC}(Z_1(U)) = \sum_{p=1}^{4} \eta_{CPC}(Z_1(pU)) \cdot C_p(Z_1(U)) \tag{4}$$

Here, $M_{CPC}(Z_1(U))$ represents the quantity obtained from the measurement result by the CPC 501 for the aerosol particles classified out based on $Z_1(U)$, $\eta_{CPC}(Z_1(pU))$ represents detection efficiency of the CPC 501 for the aerosol particles classified out based on $Z_1(pU)$, and p represents the number of charges. Therefore, the mathematical expression (4) indicates that the detection efficiency $\eta_{CPC}$ differs depending on p representing the number of charges. Note that a calibrated value of the CPC 501 means this detection efficiency $\eta_{CPC}$.

Incidentally, as described by using FIG. 6 above, since the aerosol particles classified out by the DMA 300 based on the electrical mobilities Z(U) to Z(4U) also include multiply charged ones, they are also included in the measurement results M1 to M4 by the FCAE 401 or the CPC 501.

Figure 9:
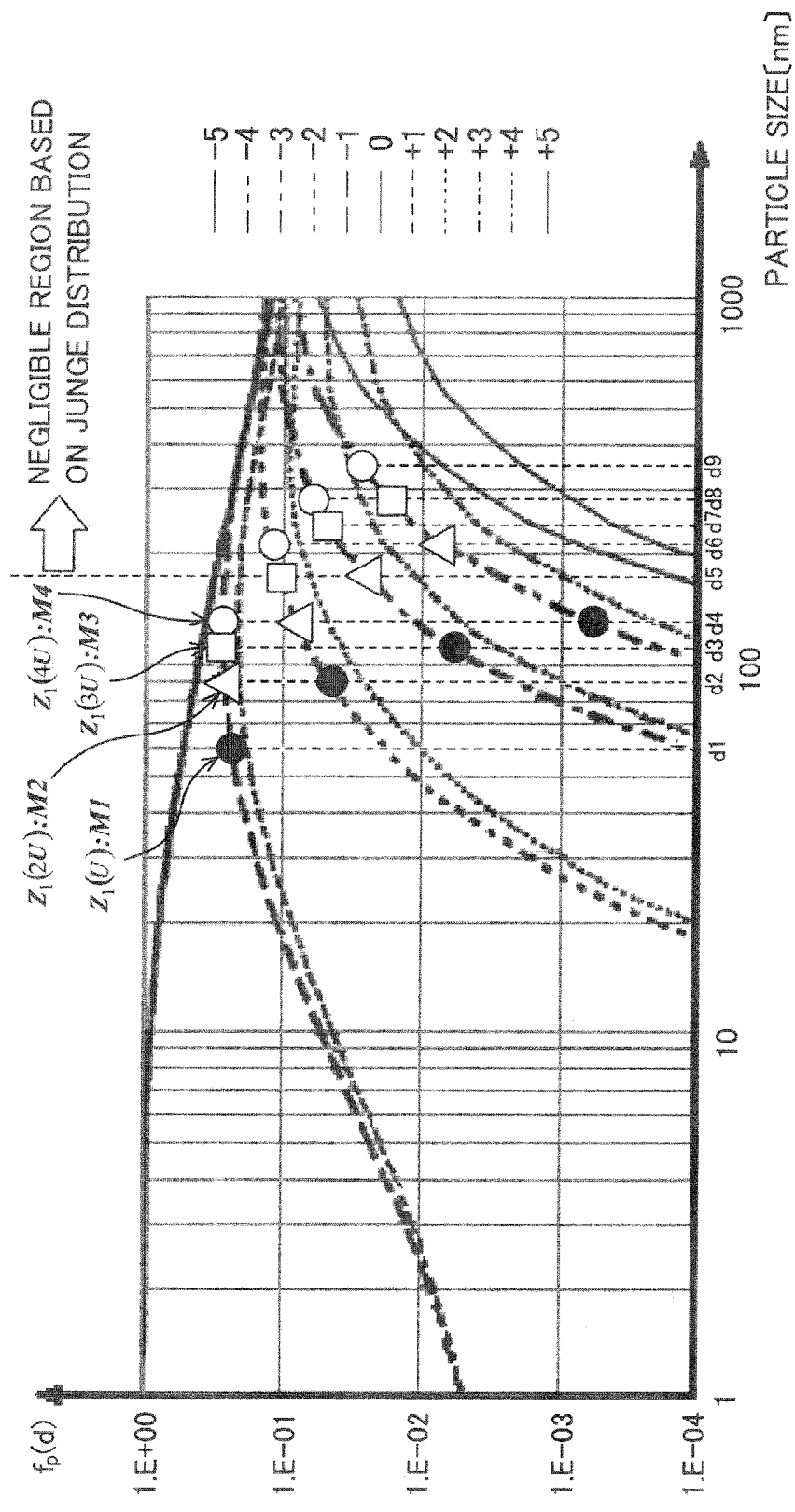
FIG. 9 is an explanatory chart of charging probability distribution obtained when measurement results M1 to M4 corresponding to the particle size of and the number of charges on the aerosol particles are plotted.

FIG. 9 is a chart where the aerosol particles classified out by the DMA 300 based on the electrical mobilities Z(U) to Z(4U) are plotted in the charging probability distribution chart (FIG. 4) in correspondence to the particle size and the number of charges. Concretely, the charging probability of the singly charged aerosol particles with the particle size $d_4$ classified out based on the electrical mobility $Z_1(4U)$ (○) is 30%, and the charging probability of doubly charged aerosol particles with the particle size $d_5$ classified out based on the electrical mobility $Z_1(3U)$ (□) is approximately 10%. For example, if the number of the singly charged aerosol particles with the particle size $d_4$ classified out based on the electrical mobility $Z_1(4U)$ (○) is negligibly small, the doubly charged aerosol particles whose particle size is $d_5$ larger than $d_4$ and which are classified out based on the electrical mobility $Z_1(3U)$ (□) and the doubly charged aerosol particles with a large number of charges and with the particle size $d_4$ classified out based on the electrical mobility $Z_1(2U)$ (Δ) are also negligible.

Further, a function expressing the charging probability is defined as $f_p(Z_1(nU))$. A relationship among the distribution functions of aerosol particles corresponding to the respective numbers of charges, classified out based on the different electrical mobilities Z is expressed by the following mathematical expressions (5). Here, p represents the numbers of charges and nU represents the supplied voltage. For example, among aerosol particles with the particle size $d_4$ in the charged equilibrium state classified out based on the electrical mobility $Z_1(4U)$, the charging probability function of the singly charged aerosol particles with the particle size $d_4$ (○) is expressed as $f_1(Z_1(4U))$, and the charging probability function of the fourfold charged aerosol particles with the particle size $d_4$ is expressed as $f_4(Z_1(4U))$. Here, the fourfold charged aerosol particles with the particle size $d_4$ classified out based on the electrical mobility $Z_1(U)$ (●) correspond to this charging probability function $f_4(Z_1(4U))$. Further, by dividing the distribution function $C_1(Z_1(4U))$ for the singly charged aerosol particles with the particle size $d_4$ classified out based on the electrical mobility $Z_1(4U)$ by the charging probability function $f_1(Z_1(4U))$, it is possible to find the total number of particles with the particle size $d_4$, and by integrating this total number of particles and the charging probability function $f_4(Z_1(4U))$ for aerosol particles with the particle size $d_4$ to have the fourfold charge, it is possible to find the number of fourfold charged particles $C_4(Z_1(U))$ with the particle size $d_4$ classified out based on the electrical mobility $Z_1(U)$.

$$C_2(Z_1(U)) = \frac{f_2(Z_1(2U))}{f_1(Z(2U))} \cdot C_1(Z_1(2U)), \tag{5}$$

$$C_2(Z_1(2U)) = \frac{f_2(Z_1(4U))}{f_1(Z_1(4U))} \cdot C_1(Z_1(4U))$$

$$C_3(Z_1(U)) = \frac{f_3(Z_1(3U))}{f_1(Z_1(3U))} \cdot C_1(Z_1(3U))$$

$$C_4(Z_1(U)) = \frac{f_4(Z_1(4U))}{f_1(Z_1(4U))} \cdot C_1(Z_1(4U))$$

Here, if the case where M2/M1 and M3/M1 are not smaller than the to prescribed value (1%) and M4/M1 is smaller than the prescribed value is supplied to the above, since the measurement result M4 of the aerosol particles classified based on the electrical mobility $Z_1(4U)$ is negligibly small, $C_1(Z_1(4U))=0$. Similarly, $C_4(Z_1(U))=C_2(Z_1(2U))=0$.

$M_{FCAE}(Z_1(U))$ to $M_{FCAE}(Z_1(4U))$ obtained from the result when the FCAE 401 measures the aerosol particles classified out based on the electrical mobilities $Z_1(U)$ to $Z_1(4U)$ can be expressed by a mathematical expression (6) to a mathematical expression (8), considering that $M_{FCAE}(Z_1(4U))=C_1(Z_1(4U))=0$. In this manner, the singly to triply charged particles are classified out based on the electrical mobility $Z_1(U)$, and the singly charged particles are classified out based on the electrical mobilities $Z_1(2U)$ and $Z_1(3U)$.

$$M_{FCAE}(Z_1(U))=\eta_{FCAE}(Z_1(U))\cdot C_1(Z_1(U))+\eta_{FCAE}(Z_1(U))\cdot 2\cdot C_2(Z_1(U))+\eta_{FCAE}(Z_1(U))\cdot 3\cdot C_3(Z_1(U)) \tag{6}$$

$$M_{FCAE}(Z_1(2U))=\eta_{FCAE}(Z_1(U))\cdot C_1(Z_1(2U)) \tag{7}$$

$$M_{FCAE}(Z_1(3U))=\eta_{FCAE}(Z_1(U))\cdot C_1(Z_1(3U)) \tag{8}$$

Further, from the above mathematical expression (5), mathematical expression (6), mathematical expression (7), and mathematical expression (8), the following mathematical expression (9) can be derived.

$$\eta_{FCAE}(Z_1(U))\cdot C_1(Z_1(U)) = M_{FCAE}(Z_1(U)) - \tag{9}$$

$$2\cdot \frac{f_2(Z_1(2U))}{f_1(Z_1(2U))}\cdot M_{FCAE}(Z_1(2U)) - 3\cdot \frac{f_3(Z_3(3U))}{f_1(Z_1(3U))}\cdot M_{FCAE}(Z_1(3U))$$

Since only the singly charged particles are classified out based on the electrical mobilities $Z_1(2U)$ and $Z_1(3U)$, it is possible to find $M_{FCAE}(Z_1(2U))$ and $M_{FCAE}(Z_1(3U))$ from the measurement by the FCAE 401. Then, $C_1(Z_1(2U))$ is found from the mathematical expression (7), whereby $C_2(Z_1(U))$ can be found from the mathematical expression (5). Further, $C_1(Z_1(3U))$ is found from the mathematical expression (8), whereby $C_3(Z_1(U))$ can be found from the mathematical expression (5). Therefore, the numbers of the doubly and triply charged particles classified out based on the electrical mobility $Z_1(U)$ are found, so that the number of singly charged particles $\eta_{FCAE}(Z_1(U))\cdot C_1(Z_1(U))$ can be found by using the measurement result $M_{FCAE}(Z_1(U))$.

Further, by the same calculation method, the following mathematical expression (10) can be derived for the CPC 501.

$$\eta_{CPC}(Z_1(U)) \cdot C_1(Z_1(U)) = M_{CPC}(Z_1(U)) - \qquad (10)$$
$$\frac{f_2(Z_1(2U))}{f_1(Z_1(2U))} \cdot M_{CPC}(Z_1(2U)) - \frac{f_3(Z_1(3U))}{f_1(Z_1(3U))} \cdot M_{CPC}(Z_1(3U))$$

As described above, when M4/M1 is smaller than 1%, it is possible to measure the number of the aerosol particles classified out by the DMA 300 based on the electrical mobility $Z_1(U)$. The FCAE 401 or the CPC 501 measures the aerosol particles classified out based on a given electrical mobility Z, and it is possible to count the number of the aerosol particles based on the measurement results $M_{FACE}$, $M_{CPC}$ and a charging probability ratio of the charging probability functions.

As for the particle size distribution of the aerosol particles in the atmosphere, the density with respect to each particle size follows the Junge distribution, which indicates that, as for the aerosol particles whose particle size is larger than 100 nm, because the number thereof is extremely small based on the inverse cubic size distribution law, and because the measurement is based on the charging probability distribution of the aerosol particles, it almost suffices if fourfold to sixfold charged ones are measured.

When the number of the aerosol particles is counted with respect to each particle size from the measurement results M1, M2, M3, M4 in the current calculation process Step S900, the particle size distribution measuring system 1 next executes Step S1000.

Step S1000: The particle size distribution measuring system 1 confirms whether or not to measure the aerosol particles with another particle size. When it is confirmed that the aerosol particles with another particle size are to be measured (Yes), the particle size distribution measuring system 1 next executes Step S100. On the other hand, when the aerosol particles with another particle size are not to be measured (No), the particle size distribution measuring system 1 finishes the measurement of the aerosol particles in the atmosphere.

Next, the electrical mobility Z regarding the classifying of the aerosol particles in the DMA 300 will be described. The electrical mobility Z can also be derived from the structure of the DMA 300 (the radius r1 of the inner electrode, the radius $r_2$ of the outer electrode, and the distance L up to the classifying) and set items regarding the operation of the DMA 300, and is expressed by the aforesaid mathematical expression (2) when the flow rate $q_2$ of the sample gas is equal to its discharge rate $q_3$ from the exit port 350 for classifying and the flow rate $q_1$ of the sheath gas is equal to its discharge rate $q_4$ from the exit port 360 ($q_1=q_4$, $q_2=q_3$).

[Transfer Function $\Omega$]

Figure 13:
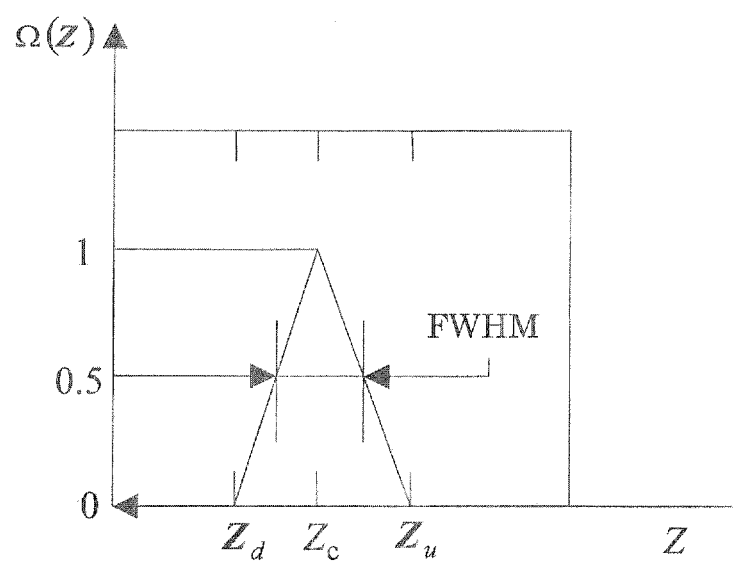
FIG. 13 is an explanatory chart of a transfer function $\Omega(Z)$ expressing a probability for the aerosol particles to be classified out based on electrical mobility Z.

Further, a probability for the aerosol particles to be actually classified out by the DMA 300, that is, a transfer function $\Omega(Z)$ is expressed as in FIG. 13.

As shown in FIG. 13, when the aerosol particles are classified out by utilizing the electrical mobility, the concentration of the aerosol particles actually classified out is an integration value of $Z_u$ to $Z_d$ expressed by the following mathematical expressions (11), In the description below, $Z_c(U)$ is substituted for $Z_1(U)$ in the aforesaid mathematical expression (2).

$$Z_c = \frac{q_1}{2\pi\Delta\Phi}, Z_d = \frac{q_1+q_2}{2\pi\Delta\Phi}, Z_u = \frac{q_1-q_2}{2\pi\Delta\Phi} \qquad (11)$$

Here, from the mathematical expression (2), $\Delta\phi = L \cdot U/\ln(r_2/r_1)$.

Therefore, the electrical mobility Z of the aerosol particles that are classified out depends on a relation of the flow rate $q_1$ of the sheath gas and the flow rate $q_2$ of the sample gas.

Further, a relational expression at a full width at half maximum (FWHM) regarding the transfer function $\Omega(Z_c)$ is expressed by the following mathematical expression (12).

$$Z_d - Z_c = Z_c - Z_u = \frac{Z_d - Z_u}{2} = \frac{q_2}{2\pi\Delta\Phi} = \frac{q_2}{q_1} \cdot Z_c \qquad (12)$$

Here, let a ratio of flow rate $\delta$ of the sheath gas $q_1$ and the sample gas $q_2$, be $\delta=q_1/q_2$, relational expressions of the electrical mobilities $Z_d$, $Z_u$ are expressed by the following mathematical expressions (13).

$$Z_d=(1+\delta)Z_c, Z_u=(1-\delta)Z_c \qquad (13)$$

Therefore, it is shown that, when the aerosol particles are classified out based on the electrical mobility $Z_c$, they are classified out from the DMA 300 while the electrical mobility has a width of $Z_d$ to $Z_u$. That is, it is shown that the narrower the width of $Z_d$ to $Z_u$ is, the more accurately the aerosol particles with the target particle size classified out based on the electrical mobility $Z_c$ can be discriminated.

Next, a case where the electrical mobilities overlap in the classifying of the aerosol particles will be described. For example, Z(U) has a relation of $Z_d(U) < Z_c(U) < Z_u(U)$ as described above. From this, it follows that Z(2U) and Z(3U) also have a relation of $Z_d(2U) < Z_c(2U) < Z_u(2U)$.

Here, a description will be given of a case where U, 2U, and 3U are supplied as the voltage V to the DMA 300 and aerosol particles are classified out based on the electrical mobilities $Z_c(U)$, $Z_c(2U)$, $Z_u(3U)$. Concretely, a description is given of the setting that prevents the mutual interference of the electrical mobilities $Z_c(U)$, $Z_c(2U)$, $Z_u(3U)$ when the number of charges being the measurement target in the particle size distribution measuring system 1 is set to up to 3.

Figure 14:
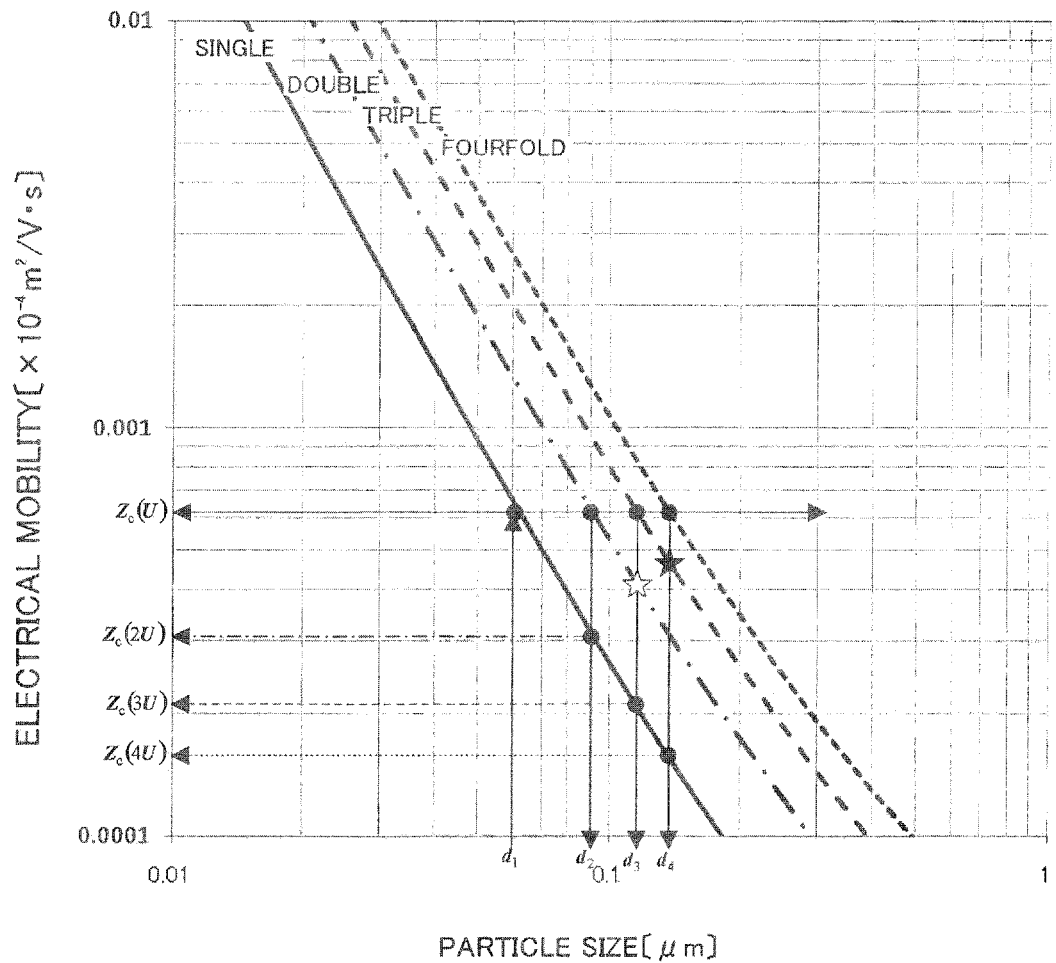
FIG. 14 is an explanatory chart of electrical mobility, and particle size and number of charge of aerosol particles that are classified out.

FIG. 14 is an explanatory chart of the particle size and the number of charge that are measured for the aerosol particles that are classified out in correspondence to the electrical mobility, while the electrical motility has a width ($\pm\delta$).

As shown in FIG. 14, the aerosol particles classified out in correspondence to the electrical mobilities $Z_c(U)$, $Z_c(2U)$, $Z_c(3U)$ are plotted in FIG. 14 as described above. Here, when the width $\delta$ of the electrical mobility is wide, doubly charged aerosol particles with the particle size $d_3$ are sometimes classified out as shown by the star mark (☆) plotted on the curve corresponding to double charge in FIG. 14. Based on the aforesaid mathematical expression (1) and mathematical expression (2), this means that aerosol particles which are classified out if a voltage (3/2)U is supplied to the DMA 300 and accordingly the aerosol particles are classified out based on electrical mobility $Z_c((3/2)U)$ are mixed.

Therefore, though the aerosol particles classified out based on the electrical mobility ($Z_c((3/2)U)$ are not measured, it is necessary to prevent the the aerosol particles classified out based on the electrical mobility ($Z_c((3/2)U)$ (☆ in FIG. 14) from mixing at the time of the measurement corresponding to $Z_c(U)$ or $Z_c(2U)$.

[Transfer Function $\Omega$ according to Electrical Mobility when Maximum Number of Charges is 3]

Figure 15:
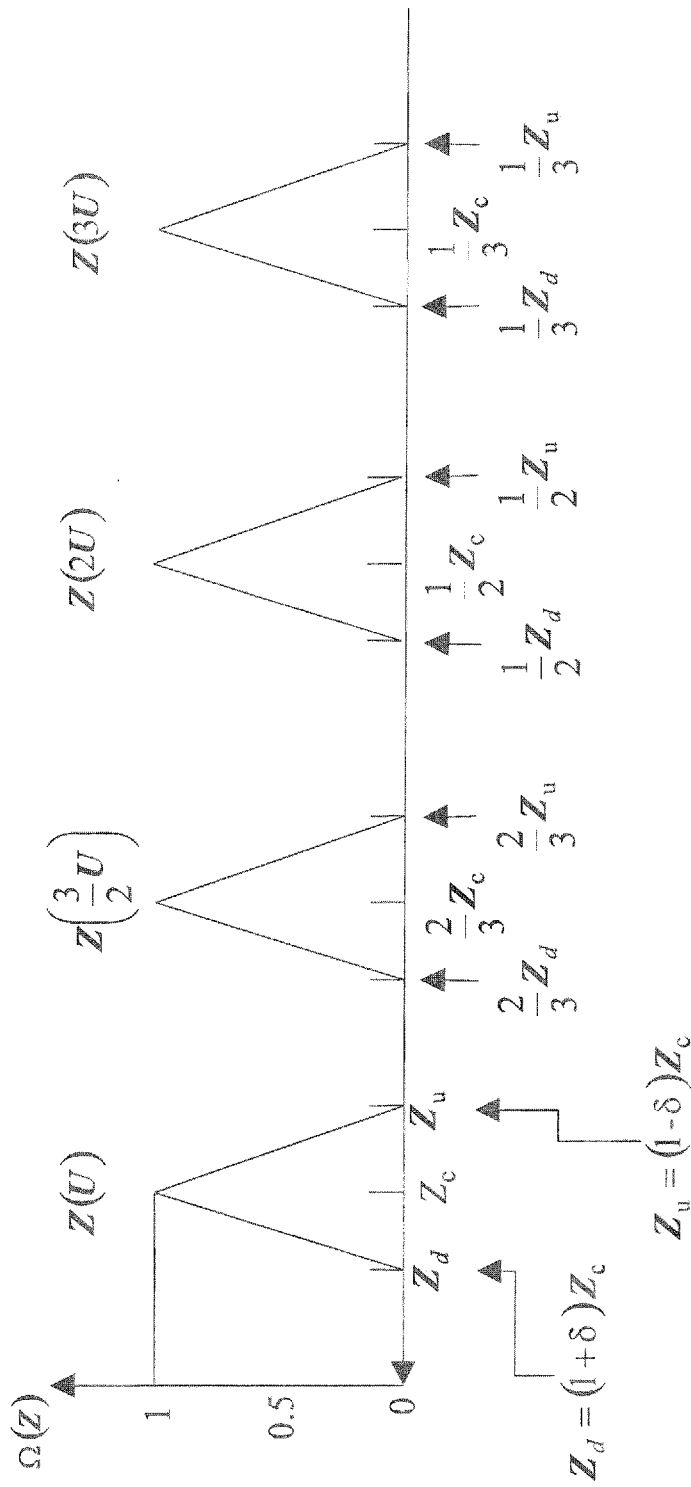
FIG. 15 is an explanatory chart of a transfer function $\Omega$ according to the electrical mobility when the maximum number of charges is 3.

FIG. 15 is a transfer function $\Omega$ necessary when the aerosol particles whose number of charges is up to 3 are measured based on the electrical mobility 4(U). The electrical mobilities $Z_c(U)$, $Z_c((3/2)U)$, $Z_c(2U)$, $Z_c(3U)$ each have a width of ±δ. Therefore, that the widths of the respective electrical mobilities do not overlap (interfere) with one another means the accurate classifying of the aerosol particles being the measurement targets, leading to the accurate calculation of the aerosol particles with respect to each particle size.

For example, in order to prevent the overlapping of the width of the electrical mobility $Z_c(U)$ and the width of $Z_c((3/2)U)$, it is necessary to satisfy the relation of $Z_c(U) > Z_d((3/2)U)$. Here, from the mathematical expression (2), $Z_c((3/2)U) = (2/3)Z_c(U)$, and according to the mathematical expression (13), $Z_d(U)$ and $Z_u(U)$ are each expressed by the mathematical expression including the ratio of flow rate δ and $Z_c(U)$, and therefore, it is understood that $(1-δ)Z_c(U) < (2/3)(1+δ)Z_c(U)$ needs to be satisfied. By solving this mathematical expression, it is possible to derive that the ratio of flow rate δ<1/5 needs to be satisfied.

Similarly, in order to prevent the overlapping of the width of the electrical mobility $Z_c((3/2)U)$ and the width of $Z_c(2U)$, it is necessary to satisfy the relation of $(2/3)(1-δ)Z_c(U) > (1/2)(1+δ)Z_c(U)$. By solving this mathematical expression, it is possible to derive that the ratio of flow rate δ<1/7 needs to be satisfied.

Similarly, in order to prevent the overlapping of the width of the electrical mobility $Z_c(2U)$ and the width of $Z_c(3U)$, it is necessary to satisfy the relation of $(1/2)(1-δ)Z_c(U) > (1/3)(1+δ)Z_c(U)$. By solving this mathematical expression, it is possible to derive that the ratio of flow rate δ<1/5 needs to be satisfied.

As described above, in order to prevent the overlapping of the widths of the electrical mobilities $Z_c(U)$, $Z_c((3/2)U)$, $Z_c(2U)$, $Z_c(3U)$, the ratio of flow rate needs to satisfy δ<1/5, δ<1/7, and δ<1/5. Therefore, if the number of charges being the measurement target in the particle size distribution measuring system 1 is set to up to 3, by making the setting satisfying the ratio of flow rate δ<1/7, the setting can prevent the overlapping of the widths of all the electrical mobilities $Z_c(U)$, $Z_c((3/2)U)$, $Z_c(2U)$. $Z_c(3U)$, which makes it possible to independently classify out the aerosol particles being the measurement targets in the DMA 300. That is, a necessary measurement value is independently obtained from the aerosol particles that are classified out, which makes it possible to further improve the accuracy in the calculation of the aerosol particles with respect to each particle size.

In the above, the description is given of the setting preventing the overlapping of the electrical mobilities when the number of charges being the measurement target in the particle size distribution measuring system 1 is set to up to 3. Next, a description will be given of the setting preventing the overlapping of the electrical mobilities when the number of charges being the measurement target is up to 4, that is, when the aerosol particles are classified out based on the electrical mobilities $Z_c(U)$, $Z_c(2U)$, $Z_c(3U)$, and $Z_c(4U)$.

As shown by the star marks (☆, ★) plotted on the curves corresponding to the single charge and the triple charge in FIG. 14 respectively, when the width of the electrical mobility is wide, there is a possibility that triply charged aerosol particles with the particle size $d_4$ are classified out in addition to doubly charged aerosol particles with the particle size $d_3$. That is, based on the aforesaid mathematical expression (1) and mathematical expression (2), this means that aerosol particles which are classified out if the voltage (3/2)U or (4/3)U is supplied to the DMA 300 and the aerosol particles are classified out based on the electrical mobilities $Z_c((3/2)U)$ or $Z_c((4/3)U)$ are mixed.

Therefore, though the aerosol particles classified out based on the electrical mobilities $Z_c((3/2)U)$ and $Z_c((4/3)U)$ are not measured, it is necessary to prevent the aerosol particles classified out based on the electrical mobilities $Z_c((3/2)U)$ and $Z_c((4/3)U)$ (☆, ★ in FIG. 14) from mixing at the time of the measurement corresponding to $Z_c(U)$ or $Z_c(2U)$.

[Transfer Function Ω according to Electrical Mobility when Maximum Number of Charges is 4]

Figure 16:
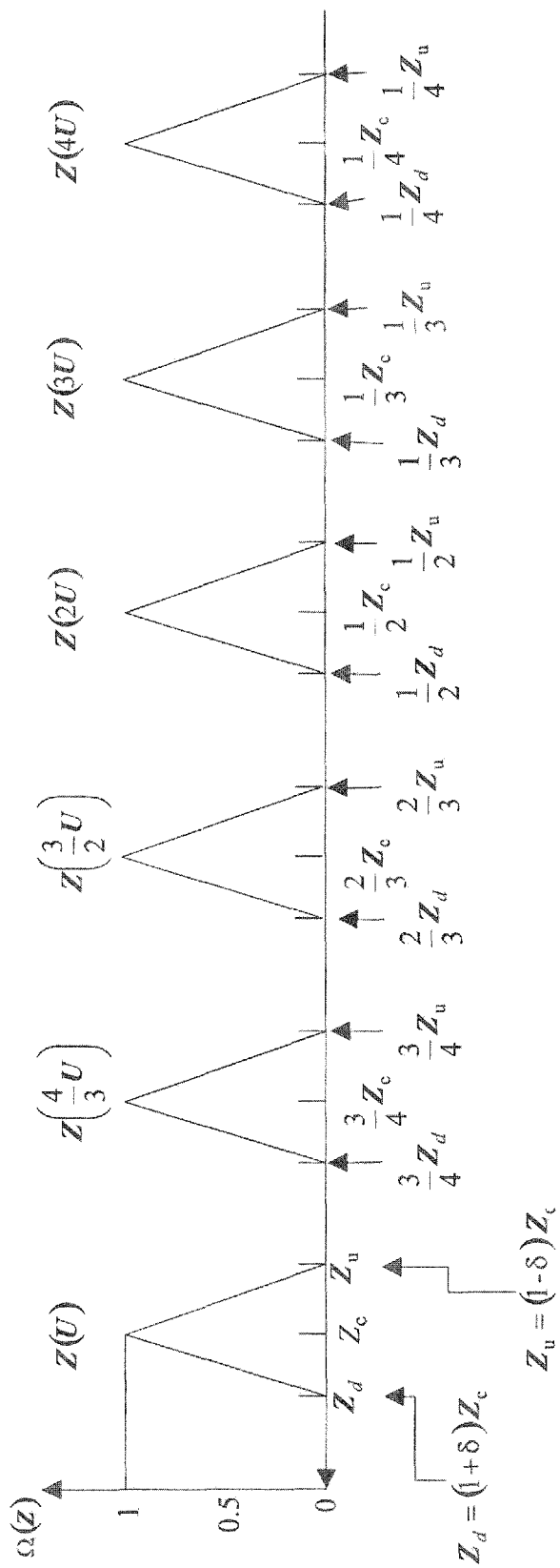
FIG. 16 is an explanatory chart of a transfer function $\Omega$ according to the electrical mobility when the maximum number of charges is 4.

FIG. 16 shows a transfer function Ω necessary when the aerosol particles whose number of charges is up to 4 are measured based on the electrical mobility $Z_c(U)$. The electrical mobilities $Z_c(U)$, $Z_c((4/3)U)$, $Z_c((3/2)U)$, $Z_c(2U)$, $Z_c(3U)$ each have a width of ±δ. Therefore, that the is widths of the respective electrical mobilities do not overlap means that the aerosol particles being the measurement targets are accurately classified out, leading to the accurate calculation of the number of the aerosol particles with respect to each particle size.

For example, it is shown that in order to prevent the overlapping of the width of the electrical mobility $Z_c(U)$ and the width of $Z_c((4/3)U)$, it is necessary to satisfy the relation of $Z_c(U) > Z_d((4/3)U)$. Here, from the mathematical expression (2), $Z_c((4/3)U) = (3/4)Z_c(U)$, and according to the mathematical expression (13), $Z_d(U)$ and $Z_u(U)$ are each expressed by the mathematical expression including the ratio of flow rate δ and Zc(U), and therefore, it is shown that $(1-δ)Z_c(U) > (3/4)(1+δ) Z_c(U)$ needs to be satisfied. By solving this mathematical expression, it is possible to derive that the ratio of flow rate δ<1/7 needs to be satisfied.

Similarly, in order to prevent the overlapping of the width of the electrical mobility $Z_c((4/3)U)$ and the width of $Z_c((3/2)U)$, it is necessary to satisfy $(3/4)(1-δ)Z_c(U) > (2/3)(1+δ)Z_c(U)$. By solving this mathematical expression, it is possible to derive that the ratio of flow rate δ<1/17 needs to be satisfied.

Similarly, in order to prevent the overlapping of the width of the electrical mobility $Z_c((3/2)U)$ and the width of $Z_c(2U)$, it is necessary to satisfy $(2/3)(1-δ)Z_c(U) > (1/2)(1+δ)Z_c(U)$. By solving this mathematical expression, it is possible to derive that the ratio of flow rate δ<1/17 needs to be satisfied.

Similarly, in order to prevent the overlapping of the width of the electrical mobility $Z_c(2U)$ and the width of $Z_c(3U)$, it is necessary to satisfy $(1/2)(1-δ)Z_c(U) > (1/3)(1+δ)Z_c(U)$. By solving this mathematical expression, it is possible to derive that the ratio of flow rate δ<1/5 needs to be satisfied.

Similarly, in order to prevent the overlapping of the width of the electrical mobility $Z_c(3U)$ and the width of $Z_c(4U)$, it is necessary to satisfy $(1/3)(1-δ)Z_c(U) > (1/4)(1+δ)Z_c(U)$. By solving this mathematical expression, it is possible to derive that the ratio of flow rate δ<1/7 needs to be satisfied.

As described above, in order to prevent the overlapping of the widths of the electrical mobilities $Z_c(U)$, $Z_c((4/3)U)$, $Z_c((3/2)U)$, $Z_c(2U)$, $Z_c(3U)$, the ratio of flow rate needs to satisfy δ<1/7, δ<1/17, δ<1/7, δ<1/5, and δ<1/7 respectively. Since the aerosol particles classified out based on the electrical mobilities Zc((4/3)U) and $Z_c((3/2)U)$ are not measured here, the widths of these electrical mobilities may overlap. That is, the ratio of flow rate need not be δ<1/17. Therefore, when the number of charges being the measurement target is set to up to 4 in the particle size distribution measuring system 1, by making the setting satisfying the ratio of flow rate δ<1/7, the setting can prevent the overlapping of the widths of all the electrical mobilities $Z_c(U)$, $Z_c((4/3)U)$, $Z_c((3/2)U)$, $Z_c(2U)$, $Z_c(3U)$ except the overlapping of the widths of the electrical mobilities $Z_c((4/3)U)$ and $Z_c((3/2)U)$, which makes it possible to execute the classifying of the aerosol particles being the measurement targets independently in the DMA 300.

In the above, the description is given of the setting preventing the overlapping of the widths of the electrical mobilities when the number of charges being the measurement target in the particle size distribution measuring system 1 is up to 3 or 4, but this is not restrictive, and it is also possible to independently classify out the aerosol particles being the measurement targets in the DMA by similarly setting the ratio of flow rate δ, also when the number of charges being the measurement targets are multiple values such as 5 or 6.

[Relation of Number of Charges on Classified Aerosol Particles and Ratio of Flow Rate]

FIG. 17 is an explanatory chart of the relation of the number of charges on the classified aerosol particles and the ratio of flow rate (ratio of flow rate=sample gas $q_2$/sheath gas $q_1$).

As shown in FIG. 17, the table shows the relation of the number of charges on the aerosol particles being measurement targets and a set ratio of flow rate $\delta=q_1/q_2$ between the sheath gas $q_1$ and the sample gas $q_2$ containing the aerosol particles, which are made to flow into the DMA 300. Concretely, it is shown that, if the number of charges being the measurement target is 2, it is necessary to make the setting satisfying the ratio of flow rate δ<1/3 in the DMA 300. Besides, it is shown that, if the number of charges being the measurement target is 5, it is necessary to make the setting satisfying the ratio of flow rate δ<1/11 in the DMA 300, and it is shown that if the number of charges being the measurement target is 6, it is necessary to make the setting satisfying the ratio of flow rate δ<1/11 in the DMA 300. Note that the ratio of flow rate can be calculated even when the number of charges being the measurement target is not limited to up to 6. Further, when the number of charges is up to 4, the electrical mobility is between the electrical mobility $Z_c(U)$ and $Z_c(2U)$ such as the electrical mobilities $Z_c((4/3)U)$ and $Z_c((3/2)U)$, but when the number of charges is 5 or more, the electrical mobility is between the electrical mobilities $Z_c(2U)$ and $Z_c(3U)$ such as the electrical mobility $Z_c((5/2)U)$, and thus is not always between the electrical mobilities $Z(U)$ and $Z_c(2U)$.

Hereafter, the contents of a method of deciding the above-described ratio of flow rate will be describe along a procedure example.

Figure 18:
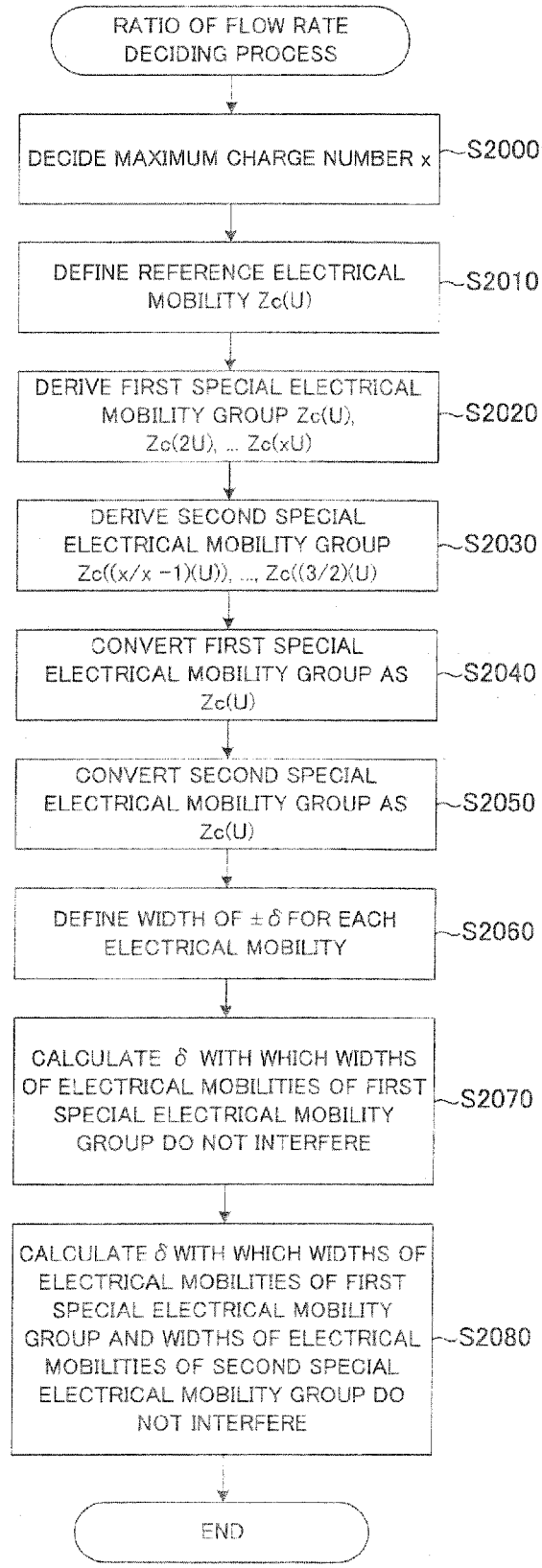
FIG. 18 is a flowchart showing a procedure example of a ratio of flow rate deciding process.

FIG. 18 is a flowchart showing a procedure example of a ratio of flow rate deciding process. The process may be executed by the control unit built in the particle size distribution measuring system 1.

Step S2000: The particle size distribution measuring system 1 decides the maximum number of charges on aerosol particles being the measurement target among the charged aerosol particles as a natural number x equal to or larger than 2. The particle size distribution measuring system 1 next executes Step S2010.

Step S2010: The particle size distribution measuring system 1 defines the electrical mobility $Z_c(U)$ serving as a reference. Concretely, Zc in the mathematical expression (11) corresponds to this. The particle size distribution measuring system 1 next executes Step S2020.

Step S2020: The particle size distribution measuring system 1 derives a first special electrical mobility group $Z_c(U)$, $Z_c(2U)$, $Z_c(3U)$, $Z_c(4U)$, . . . , $Z_c(xU)$. Concretely, when x is 3, $Z_c(U)$, $Z_c(2U)$, and $Z_c(3U)$ correspond to the first special electrical mobility group, and when x is 4, $Z_c(U)$, $Z_c(2U)$, $Z_c(3U)$, and $Z_c(4U)$ correspond to the first special electrical mobility group. The particle size distribution measuring system 1 next executes Step S2030.

Step S2030: The particle size distribution measuring system 1 derives a second special electrical mobility group $Z_c(x/(x-1))(U)$, $Z_c(x/(x-2))(U)$, . . . , $Z_c(x/2)(U)$, $Z_c((x-1)/(x-2))(U)$, $Z_c((x-1)/(x-3))(U)$, . . . , $Z_c((x-1)/2)(U)$, $Z_c((x-2)/(x-3))(U)$, $Z_c((x-2)/(x-4))(U)$, . . . , $Z_c((x-2)/2)(U)$, . . . , $Z_c(3/2))(U)$. Concretely, when x is 3, $Z_c((3/2)/U)$ corresponds to the second special electrical mobility group, and when x is 4, $Z_c((4/3)U)$ and $Z_c(3/2)U)$ correspond to the second special electrical mobility group. The particle size distribution measuring system 1 next executes Step S2040.

Step S2040: The particle size distribution measuring system 1 expresses the aforesaid first special electrical mobility group as Zc(U). Concretely, when x is 3, $Z_c(U)$, $(1/2)Z_c(U)$, and $(1/3)Z_c(U)$ correspond to the first special electrical mobility group, and when x is 4, $Z_c(U)$, $(1/2)Z_c(U)$, $(1/3)Z_c(U)$, and $(1/4)Z_c(U)$ correspond to the first special electrical mobility group. The particle size distribution measuring system 1 next executes Step S2050.

Step S2050: The particle size distribution measuring system 1 expresses the aforesaid second special electric mobility group as Zc(U). Concretely, when x is 3, $(2/3)Z_c(U)$ corresponds to the second special electrical mobility group, and when x is 4, $(3/4)Z_c(U)$ and $(2/3)Z_c(U)$ correspond to the second special electrical mobility group. The particle size distribution measuring system 1 next executes Step S2060.

Step S2060: The particle size distribution measuring system 1 defines the width ±δ of each of the electrical mobilities expressed in the previous Step S2040 and Step S2050. Concretely, each of the electrical mobilities is expressed by the mathematical expression (13). The particle size distribution measuring system 1 next executes Step S2070.

Step S2070: The particle size distribution measuring system 1 calculates δ with which the range of the electrical mobilities of the first special electrical mobility group do not interfere with one another. Concretely, when x is 3, it calculates δ with which the width of $Z_c(U)$, the width of $(1/2)Z_c(U)$, and the width of $(1/3)Z_c(U)$ as the first special electrical mobility group do not interfere with one another. As δ satisfying $(1-\delta)Z_c(U) > (1/2)(1+\delta)Z_c(U)$ and as δ satisfying $(1/2)(1-\delta)Z_c(U) > (1/3)(1+\delta)Z_c(U)$, δ<1/3 and δ<1/5 are derived respectively, and as one satisfying the two, δ<1/5 is derived.

Further, when x is 4, it calculates δ with which the width of $Z_c(U)$, the width of $(1/2)Z_c(U)$, the width of $(1/3)Z_c(U)$, and the width of $(1/4)Z_c(U)$ as the first special electrical mobility group do not interfere with one another. As δ satisfying $(1-\delta)Z_c(U) > (1/2)(1+\delta)Z_c(U)$, as δ satisfying $(1/2)(1-\delta)Z_c(U) > (1/3)(1+\delta)Z_c(U)$, and as δ satisfying $(1/3)(1-\delta)Z_c(U) > (1/4)(1+\delta)Z_c(U)$, δ<1/3, δ<1/5, and δ<1/7 are derived respectively, and as one satisfying the three, δ<1/7 is derived.

The particle size distribution measuring system 1 next executes Step S2080.

Step S2080: The particle size distribution measuring system 1 calculates δ with which the range of the electrical mobilities of the first special electrical mobility group and the range of the electrical mobilities of the second special electrical mobility group do not interfere with one another. Concretely, when x is 3, it calculates δ with which the width of $Z_c(U)$, the width of $(2/3)Z_c(U)$, and the width of $(1/2)Z_c(U)$ as the first special electrical mobility group do not interfere with one another. As δ satisfying $(1-\delta)Z_c(U) > (2/3)(1+\delta)Z_c(U)$ and as δ satisfying $(2/3)(1-\delta)Z_c(U) > (1/2)(1+$ $\delta)Z_c(U)$, $\delta<1/5$ and $\delta<1/7$ are derived respectively, and as one satisfying the two, $\delta<1/7$ is derived.

Further, when x is 4, it calculates $\delta$ with which the range $Z_c(U)$ and the width of $(3/4)Z_c(U)$ as the first special electrical mobility group do not interfere with each other, and calculates $\delta$ with which the width of $(2/3)Z_c(U)$ and the width of $(1/2)Z_c(U)$ do not interfere with each other. As $\delta$ satisfying $(1-\delta)Z_c(U)>(3/4)(1+\delta)Z_c(U)$ and as $\delta$ satisfying $(2/3)(1-\delta)Z_c(U)>(1/2)(1+\delta)Z_c(U)$, $\delta<1/7$ and $\delta<1/7$ are derived respectively, and as one satisfying the two, $\delta<1/7$ is derived.

Note that the particle size distribution measuring system 1 finally calculates $\delta$ as $\delta$ with which the widths of the adjacent electrical mobilities do not interfere with each other, based on $\delta$ calculated in the previous Step S2070 and Step S2080. Concretely, when x is 3, based on $\delta<1/5$ which is the calculation result in the previous Step S2070 and $\delta<1/7$ which is the calculation result in the previous Step S2080, it finally calculates $\delta<1/7$ as satisfying the two results. Further, when x is 4, based on $\delta<1/7$ which is the calculation result in the previous Step S2070 and $\delta<1/7$ which is the calculation result in the previous Step S2080, it finally calculates $\delta<1/7$ as satisfying the two results.

Therefore, by adjusting the flow rate of the sheath gas and the flow rate of the sample gas in the DMA 300 according to the number of charges on the aerosol particles being the measurement targets so that the condition of the final ratio of flow rate calculated above is satisfied, the aerosol particles being the measurement targets for a given electrical mobility Z are classified out accurately, which makes it possible to count the number of the aerosol particles with respect to each particle size more accurately.

What is claimed is:

1. A size-classified particle size distribution measuring method comprising:
   (A) a step of, when a sample fluid containing charged aerosol particles and a clean fluid comprised of clean air are made to flow in a predetermined electric field and when the charged aerosol particles are classified in the electric field based on electrical mobility by using a Differential Mobility Analyzer, calculating a ratio of flow rate necessary for increasing accuracy of the classification, the ratio of flow rate being a ratio between a flow rate of the sample fluid and a flow rate of the clean fluid, the step comprising:
      (a) a procedure to decide a maximum number of charges on aerosol particles being measurement targets among the charged aerosol particles as a natural number x equal to or larger than 2;
      (b) a procedure to define electrical mobility which is ability of aerosol particles whose number of charges is 1 among the aerosol particles being the measurement targets to move in the electric field, as $Zc(U)$ by using a voltage value U supplied to form the electric field;
      (c) a procedure to derive a first electrical mobility group and a second electrical mobility group based on x decided in the procedure (a), the first electrical mobility group including the electrical mobility $Zc(U)$ and electrical mobilities expressed with voltage values equal to the voltage value U multiplied by values from 2 to x respectively, and the second electrical mobility group including electrical mobilities expressed with respective voltage values equal to the voltage value U multiplied by irreducible fractions which are coprime to each other among values with regularity which are $x/(x-1)$, $x/(x-2)$, ..., $x/2$, $(x-1)/(x-2)$, $(x-1)/(x-3)$, ..., $(x-1)/2$, $(x-2)/(x-3)$, $(x-2)/(x-4)$, ..., $(x-2)/2$, ..., and $3/2$;
      (d) a procedure to express each of the electrical mobilities by using $Zc(U)$ defined in the procedure (b), regarding all the electrical mobilities included in the first electrical mobility group and the second electrical mobility group derived in the procedure (c);
      (e) a procedure to, if a range where a given electrical mobility is variable by adjusting the ratio between the flow rates of the sample fluid and the clean fluid which are made to flow in the electric field is defined as a range corresponding to the electrical mobility, define the ranges corresponding to all the electrical mobilities included in the first electrical mobility group and the second electrical mobility group derived in the procedure (c), after the procedure (d); and
      (f) a procedure to calculate the ratio between the flow rate of the sample fluid and the flow rate of the clean fluid, with which the ranges corresponding to the electrical mobilities included in the first electrical mobility group, which ranges are defined in the procedure (e), do not interfere with one another and the ranges corresponding to the electrical mobilities included in the first electrical mobility group and the ranges corresponding to the electrical mobilities included in the second electrical mobility group do not interfere with one another, whereby the sample fluid and the clean fluid are made to flow in the electric field at respective flow rates whose ratio is the calculated ratio;
   (B) a step of putting aerosol particles into a charged equilibrium state;
   (C) a step of classifying the aerosol particles charged in the step (B) in the predetermined electric field based on the electrical mobility while making the sample fluid containing the aerosol particles charged in the step (B) and the clean fluid comprised of clean air flow in the electric field based on the ratio of flow rate calculated in the step (A), the step (C) being a step of initially setting a reference voltage supplied to form the electric field to the voltage value U used for classifying aerosol particles with a predetermined particle size whose number of charges is 1, and executing a first classifying of the aerosol particles under the supplied voltage having the initially set voltage value U;
   (D) a step of measuring the aerosol particles classified out in the step (C), by an electrical or/and optical measuring method and outputting a result of the measurement as a first measurement result M1; and
   (E) a step of re-setting the voltage supplied to form the electric field, and supplying the voltage having the re-set voltage value to execute re-classifying of the aerosol particles, the step comprising:
      (g) a procedure to re-set the voltage supplied to form the electric field to nU (the voltage value U multiplied by n) for an $n^{th}$ classifying which is a sum of the voltage value of the voltage supplied in a previous classifying (previous value) and the voltage value U, and supply the voltage having the re-set voltage value to execute the re-classifying of the aerosol particles based on an electrical mobility $Zc(nU)$;
      (h) a procedure to output a new measurement result Mn which is the re-measurement result of the aerosol particles that are classified out, every time the re-classifying is executed in the procedure (g);

(i) a procedure to calculate a ratio of the measurement result Mn, which is output in the procedure (h), to the first measurement result M1; and (j) a procedure to, when the ratio calculated in the procedure (i) is larger than a prescribed value, execute the procedures (g), (h), and (i), and when the ratio calculated in the procedure (i) is equal to or smaller than the prescribed value, calculate the number of the aerosol particles with respect to each particle size from the measurement result to output a particle size distribution based on a charging probability for the aerosol particles to be charged in the step (B).

2. The size-classified particle size distribution measuring method according to claim 1, wherein in the step (C), based on that the ratio of flow rate calculated in step (A) when x being the maximum number of charges is 2 is 1/3, the flow rate of the clean fluid is set to a flow rate that is more than three times as high as the flow rate of the sample fluid.

3. The size-classified particle size distribution measuring method according to claim 1, wherein in the step (C), based on that the ratio of flow rate calculated in the step (A) when x being the maximum number of charges is 3 or 4 is 1/7, the flow rate of the clean fluid is set to a flow rate that is more than seven times as high as the flow rate of the sample fluid.

4. The size-classified particle size distribution measuring method according to claim 1, wherein in the step (C), based on that the ratio of flow rate calculated in the step (A) when x being the maximum number of charges is 5 or 6 is 1/11, the flow rate of the clean fluid is set to a flow rate that is more than eleven times as high as the flow rate of the sample fluid.

5. A particle size distribution measuring system comprising:

a ratio of flow rate deciding device in which, when a sample fluid containing charged aerosol particles and a clean fluid comprised of clean air are made to flow in a predetermined electric field and when the charged aerosol particles are classified in the electric field based on electrical mobility by using a Differential Mobility Analyzer, a ratio of flow rate necessary for increasing accuracy of the classification, which ratio is a ratio between a flow rate of the sample fluid and a flow rate of the clean fluid, is calculated, wherein the ratio of flow rate deciding device calculates the ratio of flow rate by executing:

(A) a procedure to decide a maximum number of charges on aerosol particles being measurement targets among the charged aerosol particles as a natural number x equal to or larger than 2;

(B) a procedure to form the electric field by supplying a voltage, and define electrical mobility which is ability of aerosol particles whose number of charges is 1 among the aerosol particles being the measurement targets to move in the electric field, as $Zc(U)$ by using a voltage value U of the supplied voltage;

(C) a procedure to derive a first electrical mobility group and a second electrical mobility group based on x decided in the procedure (A), the first electrical mobility group including the electrical mobility $Zc(U)$ and electrical mobilities expressed with voltage values equal to the voltage value U multiplied by values from 2 to x respectively, and the second electrical mobility group including electrical mobilities expressed with respective voltage values equal to the voltage value U multiplied by irreducible fractions which are coprime to each other among values with regularity which are $x/(x-1)$, $x/(x-2)$, ..., $x/2$, $(x-1)/(x-2)$, $(x-1)/(x-3)$, ..., $(x-1)/2$, $(x-2)/(x-3)$, $(x-2)/(x-4)$, ..., $(x-2)/2$, ..., and $3/2$;

(D) a procedure to express each of the electrical mobilities by using $Zc(U)$ defined in the procedure (B), regarding all the electrical mobilities included in the first electrical mobility group and the second electrical mobility group derived in the procedure (C);

(E) a procedure to, if a range where a given electrical mobility is variable by adjusting the ratio between the flow rates of the sample fluid and the clean fluid which are made to flow in the electric field is defined as a range corresponding to the electrical mobility, define the ranges corresponding to all the electrical mobilities included in the first electrical mobility group and the second electrical mobility group derived in the procedure (C), after the procedure (D); and (F) a procedure to calculate the ratio between the flow rate of the sample fluid and the flow rate of the clean fluid, with which the ranges corresponding to the electrical mobilities included in the first electrical mobility group, which ranges are defined in the procedure (E), do not interfere with one another and the ranges corresponding to the electrical mobilities included in the first electrical mobility group and the ranges corresponding to the electrical mobilities included in the second electrical mobility group do not interfere with one another, whereby the sample fluid and the clean fluid are made to flow in the electric field at respective flow rates whose ratio is the calculated ratio;

a neutralizer which puts the aerosol particles into a charged equilibrium state;

the Differential Mobility Analyzer which classifies the aerosol particles charged by the neutralizer in the predetermined electric field based on electrical mobility while making the sample fluid containing the aerosol particles charged by the neutralizer and the clean fluid comprised of clean air flow in the electric field based on the ratio of flow rate calculated by the ratio of flow rate deciding device, and which, in a state where a reference voltage supplied to form the electric field is initially set to the voltage value U used for classifying aerosol particles with a predetermined particle size whose number of charges is 1, executes a first classifying of the aerosol particles under the supplied voltage having the initially set voltage value U;

an aerosol particle measuring device which measures the aerosol particles classified out by the Differential Mobility Analyzer, by an electrical or/and optical measuring method and which outputs a result of the measurement as a first measurement result M1; and a measurement result analyzing device which re-sets the voltage supplied to form the electric field, and supplies the voltage having the re-set voltage value to the Differential Mobility Analyzer to cause the Differential Mobility Analyzer to execute re-classifying of the aerosol particles, the measurement result analyzing device:

(a) causing the Differential Mobility Analyzer, in a state where the voltage supplied to form the electric field is re-set to nU (the voltage value U multiplied by n) for an $n^{th}$ classifying which is a sum of the voltage value of the voltage supplied in a previous classifying (previous value) and the voltage value U, to execute the re-classifying of the aerosol particles based on an electrical mobility Zc(nU) under the supplied voltage having the re-set voltage value;

(b) causing the aerosol particle measuring device to output a new measurement result Mn which is the re-measurement result of the aerosol particles that are classified out, every time the re-classifying is executed in the (a) by the Differential Mobility Analyzer;

(c) calculating a ratio of the measurement result Mn, which the aerosol particle measuring device is caused to output in the (b), to the first measurement result M1; and (d) when the ratio calculated in the (c) is larger than a prescribed value, executing the (a), (b), and (c), and when the ratio calculated in the (c) is equal to or smaller than the prescribed value, calculating the number of the aerosol particles with respect to each particle size from the measurement result to output a particle size distribution based on a charging probability for the aerosol particles to be charged by the neutralizer.

6. The particle size distribution measuring system according to claim 5, wherein, as for the flow of the sample fluid and the clean fluid in the Differential Mobility Analyzer, based on that the ratio of flow rate calculated by the ratio of flow rate deciding device when x being the maximum number of charges is 2 is 1/3, the flow rate of the clean fluid is set to a flow rate that is more than three times as high as the flow rate of the sample fluid.

7. The particle size distribution measuring system according to claim 5, wherein, as for the flow of the sample fluid and the clean fluid in the Differential Mobility Analyzer, based on that the ratio of flow rate calculated by the ratio of flow rate deciding device when x being the maximum number of charges is 3 or 4 is 1/7, the flow rate of the clean fluid is set to a flow rate that is more than seven times as high as the flow rate of the sample fluid.

8. The particle size distribution measuring system according to claim 5, wherein, as for the flow of the sample fluid and the clean fluid in the Differential Mobility Analyzer, based on that the ratio of flow rate calculated by the ratio of flow rate deciding device when x being the maximum number of charges is 5 or 6 is 1/11, the flow rate of the clean fluid is set to a flow rate that is more than eleven times as high as the flow rate of the sample fluid.

* * * * *